(12) United States Patent
Wahlberg et al.

(10) Patent No.: US 7,601,518 B2
(45) Date of Patent: Oct. 13, 2009

(54) SECRETION OF NEUBLASTIN

(75) Inventors: Lars U. Wahlberg, Asnaes (DK); Mette Gronborg, Copenhagen NV (DK); Philip Kusk, Lynge (DK); Jens Tornoe, Copenhagen O (DK)

(73) Assignee: NsGene A/S, Ballerup (DK)

( * ) Notice: Subject to any disclaimer, the term of this patent is extended or adjusted under 35 U.S.C. 154(b) by 253 days.

(21) Appl. No.: 10/864,891

(22) Filed: Jun. 10, 2004

(65) Prior Publication Data

US 2005/0089960 A1 Apr. 28, 2005

(30) Foreign Application Priority Data

Jun. 10, 2003 (DK) ............................... 2003 00861

(51) Int. Cl.
*C12P 21/00* (2006.01)
*C12N 15/63* (2006.01)
*C12N 15/85* (2006.01)
*C07H 21/04* (2006.01)
*C07K 5/00* (2006.01)
*C07K 14/00* (2006.01)

(52) U.S. Cl. .................. 435/70.1; 435/320.1; 435/325; 435/368; 536/23.1; 530/300

(58) Field of Classification Search ........................ None
See application file for complete search history.

(56) References Cited

U.S. PATENT DOCUMENTS

| 6,361,771 B1 | 3/2002 | Tao et al. |
| 2005/0158824 A1 | 7/2005 | Pederson et al. |

FOREIGN PATENT DOCUMENTS

| WO | 9306116 | 4/1993 |
| WO | 9708196 | 3/1997 |
| WO | 0001815 | 1/2000 |
| WO | 0004050 | 1/2000 |
| WO | 0018799 | 4/2000 |
| WO | WO 0052158 A1 * | 9/2000 |
| WO | WO 01/47946 A2 | 5/2001 |
| WO | 02051433 | 7/2002 |
| WO | 02060929 | 8/2002 |
| WO | 02072826 | 9/2002 |
| WO | WO 02/078730 | 10/2002 |
| WO | WO 02/078730 A2 | 10/2002 |
| WO | 2004/094592 | 11/2004 |
| WO | 2004/108760 | 12/2004 |
| WO | 2005/039643 | 5/2005 |

OTHER PUBLICATIONS

Baudet et al., Development 127: 4335-4344, 2000.*
Bonde et al., Neuroreport 11:4069-4073, 2000.*
Wells, Biochemistry 29:8509-8517, 1990.*
Ngo et al., The Protein Folding Problem and Tertiary Structure Prediction, pp. 492-495, 1994.*
Bork, Genome Research 10:398-400, 2000.*
Skolnick et al., Trends in Biotech. 18(1):34-39, 2000.*
Doerks et al., Trends in Genetics 14:248-250, 1998.*
Smith et al., Nature Biotechnology 14:1222-1223, 1997.*
Brenner, Trends in Genetics 15:132-133, 1999.*
Bork et al., Trends in Genetics 12:425-427, 1996.*
Merlo et al., Cell Growth & Differentiation 1: 463-472, 1990.*
Palmiter et al. PNAS 88: 478-484, 1991.*
Hall et al. JBC 265: 19996-19999, 1990.*
Lone Fjord-Larsen et. al., "Efficient in vivo protection of nigral dopaminergic neurons by lentiviral gene transfer of a modified Neurturin construcct", Experimental Neurology, pp. 1-12, Mar. 21, 2005.
Mart Saarma et. al., "GDNF—a stranger in the TGF-β superfamily?", *European Journal of Biochemistry*, vol. 267, pp. 6968-6971, Feb. 2000.
Robert J. Baloh et al., "Functional mapping of Receptor Specificity Domains of Glial Cell Line-derived Neurotrophic Factor (GDNG) Family Ligands and Production of GFRα1 RET-specific Agonists", *The Journal of Biological Chemistry*, vol. 275, No. 5, pp. 3412-3420, Feb. 4, 2000.
Aebischer, et al., "Intrathecal delivery of CNTF using encapsulated genetically modified xenogeneic cells in amyotrophic lateral sclerosis patients", *Nature Medicine*, vol. 2, No. 6, pp. 696-699, Jun. 1996.
Aebischer, et al., "Recombinant proteins for neurodegenerative diseases: the delivery issue", *Trends in Neurosciences*, vol. 24, No. 9, pp. 533-540, Sep. 2001.
Bendtsen, et al., "Improved Prediction of Signal Peptides: SignalP 3.0", *J. Mol. Biol.*, vol. 340, pp. 783-795, 2004.
Hoane, et al., "Mammalian-Cell-Produced Neurturin (NTN) Is More Potent Than Purified *Escherichia coli*-Produced NTN", *Experimental Neurology*, vol. 162, pp. 189-193, 2000.
Li, et al., "Expression, purification, and characterization of recombinant human neurturin secreted from the yeast *Pichia pastoris*", *Protein Expression and Purification*, vol. 30, pp. 11-17, 2003.
Milbrandt, et al., "Persephin, a Novel Neurotrophic Factor Related to GDNF and Neurturin", *Neuron*, vol. 20, pp. 245-253, Feb. 1998.
Nielsen, et al., "Identification of prokaryotic and eukaryotic signal peptides and prediction of their cleavage sites", *Protein Engineering*, vol. 10, No. 1, pp. 1-6, 1997.

(Continued)

*Primary Examiner*—Jeffrey Stucker
*Assistant Examiner*—Aditi Dutt
(74) *Attorney, Agent, or Firm*—Ivor Elrifi; Sheridan K. Snedden; Mintz, Levin, Cohn, Ferris, Glovsky and Popeo, P.C.

(57) ABSTRACT

The present invention concerns improved methods and compositions for producing a Neublastin polypeptide as well as local delivery of Neublastin to specific regions of the nervous system including the central nervous system and the eye for example by gene therapy. The invention also concerns Neublastin expression constructs which do not encode a pro-region of a Neublastin polypeptide, which expression construct result in increased secretion of bioactive Neublastin. The invention includes the delivery of Neublastin from transduced or transfected cells encapsulated into a macrocapsule with a semipermeable membrane. The invention further concerns mammalian cells capable of producing Neublastin in increased amounts.

47 Claims, 8 Drawing Sheets

OTHER PUBLICATIONS

Nielsen, et al., "Prediction of signal peptides and signal anchors by a hidden Markov model", In. J. Glasgow et al., Eds., *Proc. Sixth Int. Conf. on Intelligent Systems for Molecular Biology*, pp. 1-9, 1998.

Rosenblad, et al., "In Vivo Protection of Nigral Dopamine Neurons by Lentiviral Gene Transfer of the Novel GDNF-Family Member Neublastin/Artemin", *Molecular and Cellular Neuroscience*, vol. 15, pp. 199-214, 2000.

Tseng, et al., "Neurturin protects dopaminergic neurons following medial forebrain bundle axotomy", *Neuroreport*, vol. 9, pp. 1817-1822, Jun. 1, 1998.

\* cited by examiner

Fig. 1

| | | | |
|---|---|---|---|
| Human IgSP | 1 | ▓dct▓r▓lf▓v▓aa▓▓tha | SEQ ID NO 1 |
| Rhesus monkey | 1 | ▓khl▓ffll▓v▓aprwvls | SEQ ID NO 2 |
| Marmoset IgSP | 1 | ▓dwt▓r▓fl▓v▓ta▓ahs | SEQ ID NO 3 |
| Mouse IgSP | 1 | ▓kcs▓v▓ff▓m▓vv▓▓vns | SEQ ID NO 4 |
| Pig IgSP | 1 | ▓efrlnwvv▓f▓llq▓vqg | SEQ ID NO 5 |
| Rat IgSP | 1 | ▓kcs▓i▓lf▓m▓lt▓▓vns | SEQ ID NO 6 |

(a)

(b)

(c)

(a)

(b)

Lane 1: ARPE-19 transfected with pNS1n-IgSP.NBN

Lane 2: ARPE-19 transduced with LV-sC.IgSP.NBN.w

Lane 3: CHO-NBN25c

Lane 4: CHO-NBN16

SECRETION OF NEUBLASTIN

FIELD OF INVENTION

The present invention concerns methods and compositions for producing a neublastin polypeptide as well as local delivery of neublastin to specific regions of the nervous system including the central nervous system and the eye for example by gene therapy. The invention includes the delivery of neublastin from transduced or transfected cells encapsulated into a macrocapsule with a semipermeable membrane. The invention further concerns mammalian cells capable of producing neublastin in increased amounts.

BACKGROUND OF THE INVENTION

Cells have ways to direct de novo synthesised proteins to various compartments of the cells and to the extracellular space. Signal peptides are enclosed in the coding part of the chromosomal DNA and are synthesised as part of the protein by the ribosomal apparatus. Signal peptides make up the N-terminal and cause the newly synthesised polypeptides to be directed into the rough endoplasmic reticulum. Here, the signal peptide is cleaved from the polypeptide and the mature protein is secreted into the surroundings. Thus, the signal peptide remains inside the cell.

The pro-part of the protein is cleaved from the mature part of the protein and ends outside the cell. For some neurotrophic factors, e.g. NGF, the pro-part of the protein is bioactive as a neuropeptide.

In gene therapy where the inserted gene codes for a protein which is to be secreted a signal sequence will need to be placed in front of the mature protein to ensure it's proper processing through the rough endoplasmic reticulum and the Golgi Apparatus. The first choice is almost invariably the native signal sequence of the protein in question, because it is generally desired that the protein is secreted and/or processed in the same way as it is secreted and processed by the native cell. For some uses it is also desired that the amount of protein expressed is the same as in the native cell. Furthermore, one cannot exclude the possibility that the cleaved signal sequence plays a role in the metabolism of the cell. Finally one of skill in the art would chose to use the pre-pro-part protein to ensure correct processing and folding of the mature protein.

In many cases it has turned out that in vivo transduced and transfected cells which are supposed to secrete a therapeutic factor do not secrete the therapeutic factor in therapeutically sufficient quantities and for sufficient time. This may also be a problem in ex vivo gene therapy where cells are transfected or transduced outside the body and inserted into the patient after genetic modification.

The prior art does not provide much information concerning the coupling of signal peptide with heterologous proteins in mammals. For heterologous expression of mammalian proteins in fungi or yeast it is common practise to replace the mammalian signal peptide with one that is functional in the producer species.

SUMMARY OF THE INVENTION

The present invention relates to a method for producing a biologically active neublastin polypeptide, comprising culturing a cell comprising an expression vector comprising a nucleic acid comprising a promoter sequence operatively linked to a nucleotide sequence encoding a signal peptide and a neublastin polypeptide, wherein said nucleotide sequence does not encode a neublastin pro-region.

The present invention provides a solution to the problem of almost complete absence of secretion of neurotrophic factor, including neublastin, often experienced upon transduction of mammalian cells with viral vectors both in vivo and in vitro. The phenomenon is also observed for plasmid based expression vectors. For some unknown reason mammalian cells are often blocked from secreting the neurotrophic factor encoded by the vector. One possible explanation could be that correct processing of secreted proteins is cell specific. This represents a serious problem in the use of viral vector gene therapy. Today, viral vector gene therapy is considered the most preferred (if not only relevant) method for in vivo or ex vivo gene therapy because the viral vectors ensure stable integration into the genome of the transduced cell.

Furthermore the present inventors have shown that by replacing the native signal peptide of neublastin with an alternative signal peptide from Immunoglobulin heavy chain variable region, the secretion of neublastin is further enhanced, especially from transduced cells.

Furthermore the present inventors have shown that by removing the nucleotide sequence encoding the pro-region from the nucleotide sequence encoding the signal peptide as well as the neublastin polypeptide, then it is possible to express and have a higher amount of neublastin secreted, than if the pro-region is included.

It has been found that although the pro-region is necessary for many proteins to fold correctly, it is possible the produce a biologically active neublastin polypeptide without a pro-region.

In a further aspect the invention relates to the nucleotide sequence encoding the signal peptide and the neublastin polypeptide, the expression vector, a pharmaceutical composition comprising the vector according to the invention and one or more pharmaceutically acceptable adjuvants, excipients, carriers and/or diluents. The pharmaceutical composition can be used for in vivo and ex vivo gene therapy.

In a further aspect the invention relates to an isolated host cell transduced or transfected with the vector according to the invention. Such genetically modified host cells have turned out to produce unexpectedly high amounts of neublastin compared to cells transduced or transfected with vectors encoding neublastin with its native signal sequence. These transduced or transfected host cells therefore constitute a promising source of producer cells for the industrial scale production of neublastin. The neublastin-secreting cells can also be used for transplantation into mammalian subjects as a source of neublastin. One particular application is ex vivo gene therapy.

In a further aspect the invention relates to a packaging cell line capable of producing an infective vector particle, said vector particle comprising a retrovirally derived genome comprising a 5' retroviral LTR, a tRNA binding site, a packaging signal, a promoter operably linked to a polynucleotide sequence encoding a fusion protein comprising neublastin and a Immunoglobulin signal peptide, an origin of second strand DNA synthesis and a 3' retroviral LTR.

These packaging cell lines can be used for producing the viral vectors according to the invention. They can also be used for in vivo gene therapy when encapsulated and transplanted to the CNS.

In a further aspect, the invention relates to a transgenic (chimeric) non-human mammal comprising at least one cell being transduced or transfected with the vector according to the invention. Such animals which overexpress neublastin can be used for gene profiling and in the screening and development of drugs.

Preferably the transduced or transfected cell has the genotype of the individual animal, i.e. is not an allogenic or xenogenic transplant.

In a further aspect, the invention relates to an implantable cell culture device, the device comprising:

a semipermeable membrane permitting the diffusion of a neurotrophic factor therethrough; and at least one isolated host cell according to the invention.

These capsules can be used for the local delivery of neublastin upon transplantation into the central nervous system. Localised and prolonged delivery of growth factor is a preferred administration method for the treatment of a number of CNS disorders, including but not limited to Parkinson's disease, Alzheimer's disease, Huntington's disease, stroke, and amyotrophic lateral sclerosis (ALS). The capsules can likewise be used for local and prolonged delivery of neublastin for peripheral disorders including but not limited to neuropathy and neuropathic pain. Further indications include eye disorders.

The capsules of this invention provide for the delivery of viral particles to a desired site in a patient using a capsular approach. Encapsulation of vector-producing cell lines permits continuous delivery of the viral particle to the target site, as opposed to a single infusion. In addition, repeat therapy is possible, with reduced likelihood of immune attack. The capsules have pores large enough to allow passage of viral particles released from the packaging cells, yet prevent host-cell passage into the capsule.

This capsular approach increases the safety and control of the therapy because the devices can easily be retrieved (terminating the transduction treatment) or explanted and reimplanted (modifying the treatment). Further, the chance of infection is reduced because the capsular device is not open or externalised.

Finally, because encapsulation prevents the packaging cells from migrating within the patient, and prolongs the viability of the packaging cells upon implant, fewer cells are likely to be needed for this therapy. This may be advantageous in further lowering an immune reaction in the patient.

In a further aspect the invention relates to use of the vector according to the invention as a medicament.

In a still further aspect the invention relates to use of the vector according to the invention for the preparation of a medicament for the treatment of a nervous system disorder.

In another aspect the invention relates to the use of the vector according to the invention for the preparation of a medicament for the treatment of a CNS disorder.

Furthermore, the invention relates to a method of treating a nervous system disease, said method comprising administering to an individual in need thereof:

a therapeutically effective amount of the vector of the invention; or a therapeutically effective amount of the pharmaceutical composition comprising the vector.

According to this aspect of the invention there is provided improved in vivo gene therapy methods for the treatment of nervous system diseases. As evidenced by the appended examples, transduction with the viral vectors of the present invention results in hitherto unseen secretion of the encoded neublastin and as a consequence improved therapeutic effect.

In a still further aspect the invention relates to a method of treating a nervous system disease, said method comprising transplanting to an individual in need thereof:

a therapeutically effective amount of the cells of the invention; or an implantable device according to the invention.

This aspect provides another way of treating nervous system disorders based on ex vivo gene therapy and implantation of therapeutic cells capable of secreting increased amounts of neublastin.

The currently preferred method for large-scale production of neublastin is heterologous expression in *E. coli*, subsequent lysis, extraction, purification, refolding and optionally cleavage of the protein. An alternative method which is used for production of research scale amounts includes culture of a mammalian producer cell such as CHO cells secreting correctly processed and folded neublastin into the culture medium, from where it can be isolated relatively easily. The mammalian cells of the present invention produce neublastin in higher amounts than seen before for mammalian cells and therefore represent an improved source of cells for producing bioactive neublastin, which is correctly processed and folded neublastin.

BRIEF DESCRIPTION OF THE DRAWINGS

FIG. 1: Alignment of IgSP sequences from various mammals.

FIG. 7.

FIG. 8.

DEFINITIONS

Figure 2:
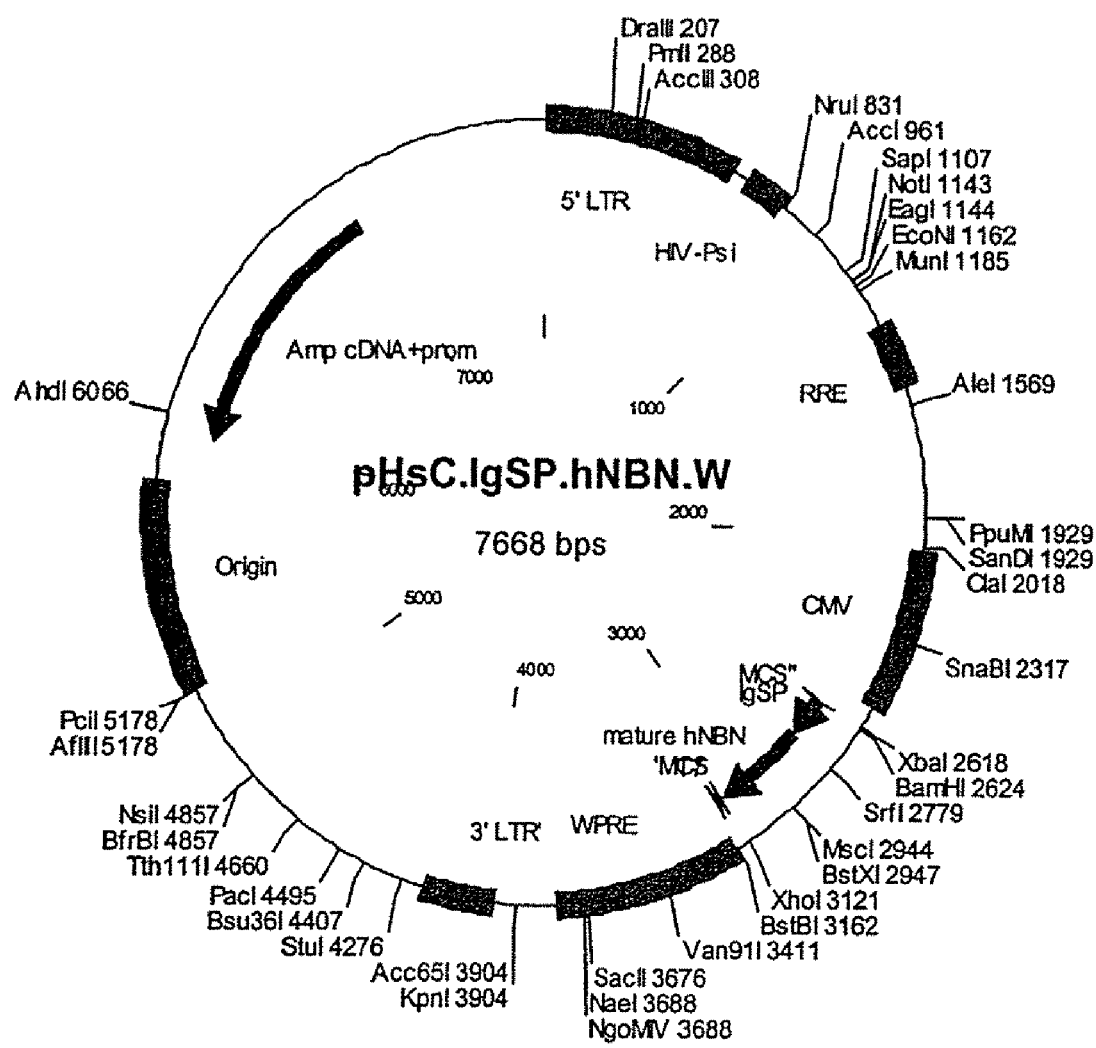
FIG. 2: Vector map of the lentiviral vector construct pHsC.IgSP.hNBN.W used for transduction experiments in Example 2.

"Neublastin pro-region" means a region comprising at least amino acids corresponding to amino acids −41 to −11 of SEQ ID NO: 10, 11, 12.

Signal peptide—eukaryotic signal peptide. A eukaryotic signal peptide is a peptide present on proteins that are destined either to be secreted or to be membrane components. It is usually N-terminal to the protein. In the present context, all signal peptides identified in SignalP (version 2.0 or preferably version 3.0) are considered a signal peptide.

A mammalian signal peptide is a signal peptide derived from a mammalian protein secreted through the ER.

Mature human neublastin polypeptide as used herein means the C-terminal 113 amino acids of native human neublastin, i.e. amino acids 28-140 of SEQ ID No. 10.

Mature mouse neublastin polypeptide as used herein means the C-terminal 113 amino acids of native mouse neublastin, i.e. amino acids 32-144 of SEQ ID No. 11.

Mature rat neublastin polypeptide as used herein means the C-terminal 113 amino acids of native rat neublastin, i.e. amino acids 32-144 of SEQ ID No. 12.

Neublastin polypeptide: as used herein means a polypeptide comprising the C-terminal 99-113 amino acids of native human neublastin, the C-terminal 99-113 amino acids of native rat neublastin, or the C-terminal 99-116 amino acids of mouse neublastin, each with up to 15 amino acid substitutions in the native sequence. In certain contexts it will be understood that "secreted neublastin polypeptide" means a polypeptide to be secreted as opposed to one that has been secreted already. The secreted neublastin polypeptide does not contain a functional neublastin pro-domain.

Functional neublastin prodomain is a peptide located between the signal peptide and the mature peptide, which propeptide is cleavable from the mature peptide by furin after cleavage of the signal peptide.

Bioactivity: ability to bind when dimerised along with GFRα3 to RET and induce RET dimerisation and autophosphorylation. Measured with Kira Elisa or RET L3 Elisa assays.

Heterologous signal peptide—a signal peptide not naturally being operatively linked to a neublastin polypeptide.

DETAILED DESCRIPTION OF THE INVENTION

The invention relates to a method for producing a neublastin polypeptide wherein the nucleotide sequence encoding neublastin polypeptide does not encode a pro-region. In the present context a pro-region comprises at least amino acids −41 to −11 of SEQ. ID. NO.: 10, 11 or 12. More preferably the pro-region comprises at least amino acids −41 to −1 of any of SEQ. ID. NO.: 10, 11 or 12. More preferably the pro-region comprises at least amino acids −41 to 10 of any of SEQ. ID. NO.: 10, 11 or 12, most preferably it comprises the pro-domain of the sequences, corresponding to amino acids −41 to 27 of SEQ ID NO: 10, or amino acids −41 to 31 of SEQ ID NO: 11, or of SEQ ID NO: 12.

Signal Peptides

The expression vector according to the invention comprises a nucleic acid comprising a promoter sequence capable of directing expression of a nucleotide sequence encoding a signal peptide operatively linked to a neublastin polypeptide, wherein said nucleotide sequence does not encode a neublastin pro-region.

The signal peptide may be any functional signal peptide, such as a heterologous signal peptide, such as an Immunoglobulin Signal Peptide. The signal peptide may be from any suitable species, such as human, mouse, rat, monkey, pig.

As evidenced by the appended examples the use of this signal peptide in general results in an improved secretion of neublastin both in vitro and in vivo. The results were reproducible both with lentivirus-transduced cells (in vivo and in vitro) and with plasmid transfected cells (in vitro). The cells produce the mature protein as a biologically active protein when the IgSP gene is fused directly to the gene coding for the mature protein (i.e. excluding the pre-pro part).

Immunoglobulin signal peptide (IgSP) is a small 19 amino acid peptide known from a large group of mammals. The sequences from human, rhesus monkey, marmoset, rat, mouse and pig are aligned in FIG. 1. The percent sequence identity compared to human IgSP varies from 21 (pig) to 68 (marmoset) percent. This relatively large variation indicates that the specific sequence can be altered to a large extent without substantially changing the biological function of the signal peptide. It is also observed that there is cross species reactivity as evidenced by the appended examples. These were carried out with the mouse IgSP which was functional in rat (in vivo experiments) and in human cells (ARPE-19 cells).

Preferably the IgSP is of mouse or human origin because the mouse IgSP is known to be functional in mouse, rat and human beings. For use in human beings, the IgSP preferably is of human origin in order to reduce the risk of any cross species side effect.

In another embodiment the signal peptide is a native (neublastin signal peptide) such as a native human neublastin signal peptide. In this context the latter construct of native neublastin signal peptide and a neublastin polypeptide is called delta-proneublastin.

Neublastin

Neublastin polypeptides are proteins, which promote survival, maintain phenotypic differentiation, prevent degeneration, promote regeneration, and restore the activity of neuronal cells and tissues. Neublastin (initially described, e. g., in WO 00/01815) has alternately been referred to as "artemin" (see, e. g., WO 00/18799) and "enovin" (see, e. g., WO 00/04050).

Neublastin has been classified as a distant member of the TGF-β superfamily (Massague, et al,. 1994, Trends in Cell Biology, 4: 172-178) and is a member of glial cell line-derived neurotrophic factor ligand family ("GDNF"; WO 93/06116), in the family which includes GDNF, persephin ("PSP"; Milbrandt et al., 1998, Neuron 20: 245253) and neurturin ("NTN"; WO 97/08196). The ligands of the GDNF subfamily have in common their ability to induce signalling through the RET receptor tyrosine kinase. These three ligands of the GDNF subfamily differ in their relative affinities for a family of neurotrophic receptors, the GFR[alpha] receptors. Neublastin acts preferably through the GFR[alpha]3-RET complex. Baudet et al., Development, 127, pp. 4335-44 (2000); Baloh et al., Neuron, 21, pp. 1291-1302 (1998); Airaksinen et al., Mol. Cell. Neuroscience, 13, pp. 313-325 (1999).

An amino acid sequence comparison of neublastin (SEQ ID NO: 10) to the GDNF subfamily members Neurturin, Persephin and GDNF is shown in Table 1. Neublastin polypeptides useful in this invention preferably hold the GDNF subfamily fingerprint, i.e. the amino acid residues underlined in Table 1.

TABLE 1

Amino Acid Sequence Comparison of neublastin to Persephin, Neurturin, and GDNF

```
Neurturin-full   ------------------MQRWKAAALASVLCSSVLSIWMCREGLLLSHRLGPA
Neublastin       MELGLGGLSTLSHCPWPRRQPALWPTLAALALLSSVAEASLGSAPRSPAPREGPPP
```

TABLE 1-continued

Amino Acid Sequence Comparison of neublastin to Persephin, Neurturin, and GDNF

```
Persephin-full    ------------------------------------------------------------
GDNF_HUMAN-full   -----MKLWDVVAVCLVLLHTASAFPLPAGKRPPEAPAEDRSLGRRRAPFALSSDS Neurturin-full    LVPLHRLPRTLDARIARLAQYRALLQGAPDAMELRELTPWAGRPPGPRRRAGRRR
Neublastin        VLASPAGHLPGGRTARWCSGRARRPPPQPSRPAPPPPAPPSALPRGGRAARAGGPG
Persephin-full    -MAVGKFLLGSLLLLSLQLGQGWGPDARGVPVADGEFSSEQVAKAGGTWLGTHRPL
GDNF_HUMAN-full   NMPEDYPDQFDDVMDFIQATIKRLKRSPDKQMAVLPRRERNRQAAAANPENSRGKG Neurturin-full    RARARLGARPCGLRELEVRVSELGLGYASDETVLFRYCAGACEA-AARVYDLGLRR
Neublastin        SRARAAGARGCRLRSQLVPVRALGLGHRSDELVRFRFCSGSCRR-ARSPHDLSLAS
Persephin-full    ARLRRALSGPCQLWSLTLSVAELGLGYASEEKVIFRYCAGSCPRGARTQHGLALAR
GDNF_HUMAN-full   RRGQRGKNRGCVLTAIHLNVTDLGLGYETKEELIFRYCSGSCDA-AETTYDKILKN
                         * *      : *  ****:  :.*  : **:*:*:*     *    :. *

Neurturin-full    LRQRRRLRRE---RVRAQPCCRPTAYEDEVSFLDAHSRYHTVHELSARECACV-
Neublastin        LLGAGALRPPPGSRPVSQPCCRPTRYE-AVSFMDVNSTWRTVDRLSATACGCLG
Persephin-full    LQGQGRAHGG--------PCCRPTRYT-DVAFLDDRHRWQRLPQLSAAACGCGG
GDNF_HUMAN-full   LSRNRRLVSD----KVGQACCRPIAFDDDLSFLDDNLVYHILRKHSAKRCGCI-
                  *                .****   :      ::*:*  .  ::  : .  **   *.*
```

\* indicates positions which have a single, fully conserved residue.
: indicates that one of the following 'strong' groups is fully conserved:
-STA, NEQK, NHQK, NDEQ, QHRK, MILV, MILF, HY, FYW.
. indicates that one of the following 'weaker' groups is fully conserved:
-CSA, ATV, SAG, STNK, STPA, SGND, SNDEQK, NDEQHK, NEQHRK, VLIM, HFY.

From the amino acid sequence alignment shown in Table 1, it can be seen that neublastin has seven cysteine residues at locations that are conserved within the TGF-[beta] superfamily. Based on this sequence alignment, neublastin was shown to be a member of the GDNF subfamily of neurotrophic factors (LGLG-FR(Y/F)CSGSC-QxCCRP-SAxxCGC, the GDNF subfamily fingerprint, underlined in Table 1).

The neublastin polypeptides useful herein may be provided in any bioactive form, including the form of pre-proteins, mature proteins, glycosylated proteins, phosphorylated proteins, truncated forms, or any other post-translationally modified protein. It is assumed that a bioactive neublastin is in the dimerized form for each NBN variant, because dimer formation is required for activity. Little to no activity is observed in a monomeric NBN polypeptide. A bioactive neublastin polypeptide includes a dimerized polypeptide that, in the presence of a cofactor (such as GFR[alpha]3 or RET), binds to GFR[alpha]3 or to a complex of GFR[alpha]3 and RET, induces dimerization of RET, and autophosphorylation of RET. Accordingly, a "neublastin polypeptide," as used herein, is a polypeptide which possesses neurotrophic activity (e.g., as described in WO 00/01815).

Neublastin in bioactive form can be detected using the RetL3 ELISA assay described in Example 1. Neublastin without biological function will not be detected by the RetL3 ELISA assay.

The following full-length sequences represent the wild type pre-pro neublastin with wild type signal peptide. Upon transduction or transfection into mammalian cells the resulting mature neublastins are only secreted in very small amounts. The native signal peptide of human, mouse and rat neublastin is represented by the first 39 amino acids.

$AA_{-80}$-$AA_{140}$ of SEQ ID NO: 10 ("wild type" human prepro), $AA_{-80}$-$AA_{144}$ of SEQ ID No. 11 (mouse prepro), $AA_{-80}$-$AA_{144}$ of SEQ ID NO: 12 (rat prepro), The following "wild-type" neublastin amino acid ("aa" or "AA") sequences are exemplary of those that are useful in the methods and compositions of this invention:

$AA_1$-$AA_{140}$ of SEQ ID NO: 10 (mature 140AA; hereafter "140NBN"), $AA_{25}$-$AA_{140}$ of SEQ ID NO: 10 (mature 116AA; hereafter "116NBN"), $AA_{28}$-$AA_{140}$ of SEQ ID NO: 10 (mature 113AA (SEQ ID No. 14); hereafter "113NBN"), $AA_1$-$AA_{144}$ of SEQ ID NO: 11 (mouse mature 144 AA), $AA_1$-$AA_{144}$ of SEQ ID NO: 12 (rat mature —144 AA), Peptides with a C-terminal sequence set forth in $AA_{107}$-$AA_{140}$ of SEQ ID No. 10, more preferably $AA_{76}$-$AA_{140}$ of SEQ ID NO. 10, and which retain the 7 Cys residues characteristic of the GDNF family and of the TGF-beta super family.

In one embodiment, the preferred neublastin polypeptide contains (seven) cysteines conserved as in SEQ ID NO. 10 at positions 43,70,74,107,108,136 and 138. These seven conserved cysteine residues are known within the TGF-superfamily to form three intramonomeric disulfide bonds (contemplated, e. g., in SEQ ID No. 10 between cysteine residues 43-108, 70-136, and 74-138) and one intermonomeric disulfide bond (contemplated, e. g., in SEQ ID NO. 10 between cysteine residues 107-107), which together with the extended beta strand region constitutes the conserved structural motif for the TGF-[beta] superfamily. See, e. g., Daopin et al., Proteins 1993,17: 176-192.

Preferably the neublastin polypeptide is one of the mature forms of the wild type protein. It is presently believed that the absence of the pro-region is important for high secretion levels in genetically modified mammalian cells.

Neublastin polypeptides useful in the present invention also include truncated forms of the full-length neublastin molecule. In such truncated molecules, one or more amino acids have been deleted from the N-terminus or the C-terminus, preferably the N-terminus. The truncated neublastin polypeptide may be obtained by providing a mature neublastin polypeptide and contacting the mature neublastin polypeptide with at least one protease under conditions sufficient to produce the truncated neublastin polypeptide. Preferably, at least one protease is an exoprotease, and contacting the mature neublastin polypeptide results in formation of an exopeptidase neublastin polypeptide digestion product that can be further digested with a dipeptidyl peptidase. More preferably according to the present invention the protein encoded by the expression vectors is the truncated form and needs no further processing.

The truncated neublastin polypeptides described herein preferably include a polypeptide sequence that encompasses the seven cysteine residues conserved in the mature neublastin sequence. In certain preferred embodiments, the truncated neublastin polypeptide includes at least the 85 carboxy terminal amino acids of mature 113NBN neublastin polypeptide. In more preferred embodiments the truncated neublastin polypeptide includes at least the 98 carboxy terminal amino acids of mature human 113 NBN.

One truncated form includes the 97 amino acids from the first to the last of the seven cysteine residues of mature neublastin. This corresponds to amino acids no 2 to 97 of SEQ ID No 20.

Other variants of neublastin include truncated NBN forms. Examples of these include:
(i) the 112AA polypeptide sequence designated herein as NBN 112, which possesses the carboxy terminal 112 amino acids of a mature neublastin polypeptide, e.g., amino acids 29-140 of SEQ ID NO. 10.
(ii) the 111 AA polypeptide sequence designated herein as NBN111, which possesses the carboxy terminal 111 amino acids of a mature neublastin polypeptide, e.g., amino acids 30-140 of SEQ ID NO. 10
(iii) the 110 AA polypeptide sequence designated herein as NBN110, which possesses the carboxy terminal 110 amino acids of a mature neublastin polypeptide, e.g., amino acids 31-140 of SEQ ID NO. 10
(iv) the 109 AA polypeptide sequence designated herein as NBN109, which possesses the carboxy terminal 109 amino acids of a mature neublastin polypeptide, e.g., amino acids 32-140 of SEQ ID NO. 10
(v) the 108AA polypeptide sequence designated herein as NBN108, which possesses the carboxy terminal 108 amino acids of a mature neublastin polypeptide, e.g., amino acids 33-140 of SEQ ID NO. 10
(vi) the 107AA polypeptide sequence designated herein as NBN107, which possesses the carboxy terminal 107 amino acids of a mature neublastin polypeptide, e.g., amino acids 34-140 of SEQ ID NO. 10
(vi) the 106AA polypeptide sequence designated herein as NBN106, which possesses the carboxy terminal 106 amino acids of a mature neublastin polypeptide, e.g., amino acids 35-140 of SEQ ID NO. 10
(viii) the 105AA polypeptide sequence designated herein as NBN105, which possesses the carboxy terminal 105 amino acids of a mature neublastin polypeptide, e.g., amino acids 36-140 of SEQ ID NO. 10
(ix) the 104AA polypeptide sequence designated herein as NBN104, which possesses the carboxy terminal 104 amino acids of a mature neublastin polypeptide, e.g., amino acids 37-140 of SEQ ID NO. 10 (also set forth as SEQ ID No. 19)
(x) the 103AA polypeptide sequence designated herein as NBN103, which possesses the carboxy terminal 103 amino acids of a mature neublastin polypeptide, e.g., amino acids 38-140 of SEQ ID NO. 10
(xi) the 102AA polypeptide sequence designated herein as NBN 102, which possesses the carboxy terminal 102 amino acids of a mature neublastin polypeptide, e.g., amino acids 39-140 of SEQ ID NO. 10
(xii) the 101AA polypeptide sequence designated herein as NBN101, which possesses the carboxy terminal 101 amino acids of a mature neublastin polypeptide, e.g., amino acids 40-140 of SEQ ID NO. 10
(xiii) the 100AA polypeptide sequence designated herein as NBN100, which possesses the carboxy terminal 100 amino acids of a mature neublastin polypeptide, e.g., amino acids 41-140 of SEQ ID NO. 10
(xiv) the 99AA polypeptide sequence designated herein as NBN99, which possesses the carboxy terminal 99 amino acids of a mature neublastin polypeptide, e.g., amino acids 42-140 of SEQ ID NO. 10 (also set forth as SEQ ID No. 20)

It is understood that the truncated forms of neublastin disclosed herein (e.g., the 112AA through 99AA forms) have neurotrophic activity.

In most preferred embodiments, the truncated neublastin polypeptide is the 99 aa, 100 aa, 101 aa, 102 aa, 103 aa, 104 aa, 105 aa, 106 aa, 107 aa, 108 aa, 109 aa, 110 aa, 111 aa or 112 aa carboxy terminal amino acids of mature 113 AA neublastin polypeptide (i. e., NBN99, NBN100, NBN101, NBN102, NBN103, NBN104, NBN105, NBN106, NBN107, NBN108, NBN109, NBN110, NBN111 or NBN112, respectively). The sequences may also be found in the mouse and rat neublastin polypeptides as the carboxy terminal 99 aa, 100 aa, 101 aa, 102 aa, 103 aa, 104 aa, 105 aa, 106 aa, 107 aa, 108 aa, 109 aa, 110 aa, 111 aa or 112 aa, respectively, in SEQ ID No. 11 and 12. These most preferred examples of truncated NBN forms are bioactive (referred to "bioactive truncated neublastin polypeptides") as they have been demonstrated to have neurotrophic activity. As stated above, NBN dimerization is required for bioactivity, as little to no activity is observed with the NBN monomeric polypeptide.

Truncated forms of the mouse and rat neublastins are also contemplated. These may consist of the C-terminal 99, 100, 101, 102, 103, 104, 105, 106, 107, 108, 109, 110, 111, 112, 113, 114, or 115 amino acids of SEQ ID No 16 (mouse) or they may consist of the C-terminal 99, 100, 101, 102, 103, 104, 105, 106, 107, 108, 109, 110, 111 or 112 amino acids of SEQ ID No 18 (rat).

The NBNs useful in this invention also include those NBN polypeptides that have an amino acid sequence with substantial similarity or identity to the various prepro, pro, mature and truncated "neublastin" polypeptides set forth above. Preferably, the neublastin polypeptide used has at least 70%, more preferably 85%, still more preferably 90%, or still further preferably 95% identity or similarity to the mature peptide of the neublastin polypeptides in SEQ ID NO. 10-20. Most preferably the neublastin polypeptide used has at least 99% similarity or identity to the mature peptides of the neublastin polypeptides in SEQ ID No. 10-20.

The degree to which a candidate polypeptide shares homology with a neublastin polypeptide of the invention is determined as the degree of similarity or identity between two amino acid sequences.

A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence, requires that, following alignment, 70% of the amino acids in the candidate sequence are identical to the corresponding amino acids in the reference sequence. Identity is determined by computer analysis, such as, without limitations, the ClustalX computer alignment program (Thompson J D, Gibson T J, Plewniak F, Jeanmougin F, & Higgins D G: "The ClustalX windows interface: flexible strategies for multiple sequence alignment aided by quality analysis tools"; Nucleic Acids Res. 1997,25 (24): 4876-82), and the default parameters suggested therein. Using this program, the mature part of a polypeptide encoded by an analogous DNA sequence of the invention exhibits a degree of identity of at least 70%, more preferably 85%, still more preferably 90%, or still further preferably 95%, most preferably at least 99% with the amino acid sequences presented herein as SEQ ID NO: 10 (human NBN), SEQ ID NOS: 11 and 12 (rodent NBN).

Other alignment tools are known, such as the dynamic programming algorithm described in Needleman et al., J. Mol. Biol. 48 : 443 (1970), and the Align Program, a commercial software package produced by DNAstar, Inc. the teachings of which are incorporated by reference herein. Once the alignment between the candidate and reference sequence is made and refined, a percent homology score is calculated. The individual amino acids of each sequence are compared sequentially according to their similarity to each other.

Similarity factors include similar size, shape and electrical charge. One particularly preferred method of determining amino acid similarities is the PAM250 matrix described in Dayhoff et al., Atlas of protein sequence and structure 345-352 (1978 & Supp.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation.

The raw score is then normalized by dividing it by the geometric mean of the scores of the candidate compound and the seven cysteine skeleton of the neublastin polypeptides. The geometric mean is the square root of the product of these scores. The normalized raw score is the percent homology.

As noted above, the neublastin polypeptides of the invention include variant polypeptides. In the context of this invention, the term "variant polypeptide" includes a polypeptide (or protein) having an amino acid sequence that differs from number of residues in the polypeptide or protein. Preferably, conservative amino acid substitutions represent changes in less than 5% of the polypeptide or protein, most preferably less than 2% of the polypeptide or protein.

The neublastin polypeptide in one embodiment comprises up to 15 amino acid substitutions, such as up to 12 amino acid substitutions, such as up to 10 amino acid substitutions, such as up to 8 amino acid substitutions, such as up to 5 amino acid substitutions. For example, when calculated in accordance, e. g., with human 113NBN, most preferred conservative substitutions would represent fewer than three amino acid substitutions in the wild type mature amino acid sequence. In a particularly preferred embodiment, there is a single amino acid substitution in the mature sequence, wherein both the substituted and replacement amino acid are non-cyclic. Other examples of particularly conservative substitutions include the substitution of one hydrophobic residue for another, such as isoleucine, valine, leucine or methionine, or the substitution of one polar residue for another, such as the substitution of arginine for lysine, glutamic for aspartic acid, or glutamine for asparagine, and the like.

The term conservative substitution also includes the use of a substituted amino acid residue in place of an un-substituted parent amino acid residue provided that antibodies raised to the substituted polypeptide also immunoreact with the un-substituted polypeptide.

Modifications of this primary amino acid sequence may result in proteins, which have substantially equivalent activity as compared to the unmodified counterpart polypeptide, and thus may be considered functional analogs of the parent proteins. Such modifications may be deliberate, e. g. as by site-directed mutagenesis, or they may occur spontaneously, and include splice variants, isoforms, homologues from other species, and polymorphisms. Such functional analogs are also contemplated according to the invention.

An alignment of 99 C-terminal amino acids from humans, mice and rats is shown below:

```
                 CLUSTAL W (1.82) multiple sequence alignment

Mouse    GCRLRSQLVPVSALGLGHSSDELIRFRFCSGSCRRARSQHDLSLASLLGAGALRSPPGSR
        Rat      GCRLRSQLVPVSALGLGHSSDELIRFRFCSGSCRRARSPHDLSLASLLDAGALRSPPGSR
        Human    GCRLRSQLVPVRALGLGHRSDELVRFRFCSGSCRRARSPHDLSLASLLGAGALRPPPGSR
                 *********** ****** ****.*********************.*****.*****

Mouse    PISQPCCRPTRYEAVSFMDVNSTWRTVDHLSATACGCLG
        Rat      PISQPCCRPTRYEAVSFMDVNSTWRTVDHLSATACGCLG
        Human    PVSQPCCRPTRYEAVSFMDVNSTWRTVDRLSATACGCLG
                 *.***********************.:**********
``` the mature peptide presented as part of SEQ ID NO. 10, 13, 14, 19, or 20 (human NBN), or SEQ ID No. 11, 12, 15-18 (rodent NBN), at one or more amino acid positions. Such variant polypeptides include the modified polypeptides described above, as well as conservative substitutions, splice variants, isoforms, homologues from other species, and polymorphisms.

As defined herein, the term "conservative substitutions" denotes the replacement of an amino acid residue by another, biologically similar, residue. Typically, biological similarity, as referred to above, reflects substitutions on the wild type sequence with conserved amino acids.

For example, one would expect conservative amino acid substitutions to have little or no effect on the biological activity, particularly if they represent less than 10% of the total Substitutions are preferably conducted at positions of non-conservancy marked with "no star", "." or ":".

Other preferred positions for substitution are denoted with "%".

Moreover, modifications of the primary amino acid sequence may result in proteins, which do not retain the biological activity of the parent protein, including dominant negative forms, etc. A dominant negative protein may interfere with the wild-type protein by binding to, or otherwise sequestering regulating agents, such as upstream or downstream components, that normally interact functionally with the polypeptide. Such dominant negative forms are also contemplated according to the invention.

Biologically active forms of truncated neublastin are known from WO 02/072826 (NsGene and Biogen). Truncated and mutated neublastin molecules are also known from WO 02/060929 (Biogen), especially mutated neublastin comprising an amino acid sequence derived from amino acids 8-113 of SEQ ID No. 14, wherein the variant neublastin polypeptide includes one or more of the amino acid substitutions selected from the group consisting of: an amino acid other than arginine at position 14 in the amino acid sequence of said variant polypeptide, an amino acid other than arginine at position 39 in the amino acid sequence of said variant polypeptide, an amino acid other than arginine at position 68 of said variant polypeptide, and an amino acid other than asparagine at position 95 of said variant polypeptide, wherein the positions of said amino acids are numbered in accordance with the polypeptide sequence of SEQ ID NO: 10. The mutated forms may be truncated as described above or include the whole length of the mature protein (amino acids 1-113 of SEQ ID NO 14). Preferably the amino acid at position 14, 39 or 68 is a lysine.

Cleavage of Signal Peptide

Before deciding on a specific neublastin form to incorporate into an expression construct, the likelihood of cleavage of the signal peptide, such as Igsp can be checked using state of the art prediction tools. One such preferred prediction tool is the SignalP software (SianalP 2.0), which is available at the SignalP WWW server, or preferred, the newer version 3.0 available from the same server.

The SignalP WWW server will return three scores between 0 and 1 for each position in your sequence:

C-score (raw cleavage site score)

The output score from networks trained to recognize cleavage sites vs. other sequence positions. Trained to be:
high at position +1 (immediately after the cleavage site)
low at all other positions.

S-score (signal peptide score)

The output score from networks trained to recognize signal peptide vs. non-signal-peptide positions. Trained to be:
high at all positions before the cleavage site at 30 positions after the cleavage site and
low in the N-terminals of non-secretory proteins.

Y-score (combined cleavage site score)

The prediction of cleavage site location is optimized by observing where the C-score is high and the S-score changes from a high to a low value. The Y-score formalizes this by combining the height of the C-score with the slope of the S-score.

Specifically, the Y-score is a geometric average between the C-score and a smoothed derivative of the S-score (i.e., the difference between the mean S-score over d positions before and d positions after the current position, where d varies with the chosen network ensemble).

All three scores are averages of five networks trained on different partitions of the data.

For each sequence, SignalP will report the maximal C-, S-, and Y-scores, and the mean S-score between the N-terminal and the predicted cleavage site. These values are used to distinguish between signal peptides and non-signal peptides. If your sequence is predicted to have a signal peptide, the cleavage site is predicted to be immediately before the position with the maximal Y-score.

For a typical signal peptide, the C- and Y-scores will be high at position +1, while the S-score will be high before the cleavage site and low thereafter.

For comparison the prediction can be compared to the predicted cleavage of the wildtype neublastin signal peptide (cleavage between amino acids no 39 and 40 of pre-pro NBN).

Preferred neublastins are those which have a predicted cleavage between the IgSP and the neublastin in either the SignalP-NN or the SignalP-HMM program. These include but are not limited to NBN113, NBN106, NBN104, NBN102, and NBN99. Particularly preferred are neublastins which have a predicted signal peptide at this position in both SignalP-NN and SignalP-HMM. These include NBN113 and NBN99.

The newer version (3.0) also includes a new score D or Dmax (Discrimination score) that describes "signal peptidedness" that is found to correlate to level of secretion using said signal peptide with the protein in question.

It is preferred that a signal peptide used in the present invention exhibits a Dmax value of at least 0.5, such as at least 0.6. such at least 0.7, such as at least 0.8, with the neublastin polypeptide selected.

References: Henrik Nielsen, Jacob Engelbrecht, Sren Brunak and Gunnar von Heijne: Identification of prokaryotic and eukaryotic signal peptides and prediction of their cleavage sites. *Protein Engineering*, 10, 1-6 (1997). For the SignalP-HMM output model: Henrik Nielsen and Anders Krogh: Prediction of signal peptides and signal anchors by a hidden Markov model. In *Proceedings of the Sixth International Conference on Intelligent Systems for Molecular Biology* (ISMB 6), AAAI Press, Menlo Park, Calif., pp. 122-130 (1998). Improved prediction of signal peptides—SignalP 3.0. Jannick Dyrlv Bendtsen, Henrik Nielsen, Gunnar von Heijne and Sren Brunak. J M B (2004). Prediction of signal peptides and signal anchors by a hidden Markov model. Henrik Nielsen and Anders Krogh. Proceedings of the Sixth International Conference on Intelligent Systems for Molecular Biology (ISMB 6), AAAI Press, Menlo Park, Calif., pp. 122-130, 1998.

Medical Use and Methods of Treatment

In one aspect the invention relates to the use of the vector according to the invention for the preparation of a medicament for the treatment of a nervous system disorder. The nervous system disorder can be a disorder of the peripheral nervous system or the central nervous system.

Neublastin is useful for treating a defect in a neuron, including without limitation lesioned neurons and traumatized neurons. Peripheral nerves that experience trauma include, but are not limited to, nerves of the medulla or of the spinal cord. Neublastin is useful in the treatment of neurodegenerative disease, e.g., cerebral ischaemic neuronal damage; neuropathy, e.g., peripheral neuropathy, Alzheimer's disease, Huntington's disease, Parkinson's disease, amyotrophic lateral sclerosis (ALS). Neublastin is further contemplated for use in the treatment of impaired memory, e.g., memory impairment associated with dementia.

Neublastin is also known as a therapeutic candidate for treating neuropathic pain in a mammal. The neuropathic pain may be associated with toxin-induced nerve damage, pathogen-induced nerve damage, trauma-induced nerve damage, drug-induced nerve damage, idiopathic neuropathy, diabetic neuropathy, inflammation-induced nerve damage, or neurodegeneration. Neublastin can also be used for treating peripheral neuropathy in a mammal. The peripheral neuropathy may include the group consisting of trauma-induced neuropathies, viral-induced neuropathies, chemotherapy-induced neuropathies, toxin-induced neuropathies, drug-induced neuropathies, vitamin-deficiency-induced neuropathies; idiopathic neuropathies; and diabetic neuropathies. Methods and compositions for treatment of neuropathic pain using neublastin are disclosed in WO 02/078730 (Biogen).

Preferably, neublastin is used for treating a disorder selected from the group consisting of peripheral neuropathy including neuropathic pain, spinal cord injury, spinal root avulsion, tic doloreaux, causalgia, corneal wounds and retinopathies.

According to one preferred embodiment of the invention the neurodegenerative disease to be treated is Parkinson's disease. Neublastin is known to increase survival of dopaminergic neurons (WO 00/01815 NsGene; Baloh et al 1998 Neuron 21:1291-1302).

The vectors, capsules, and compositions of the present invention can also be used for the treatment of eye diseases, such as retinitis pigmentosa, macular degeneration, glaucoma, and diabetic retinopathy. Neublastin may also be used in the treatment of corneal wounds and ulcers (EP 1 223 966 Biopharm)

Nervous system diseases may be treated by administering to an individual in need thereof a therapeutically effective amount of the vector of the invention; or a therapeutically effective amount of the pharmaceutical composition of the invention.

Also provided are stereotaxic coordinates for the portions of the brain to be transduced to or into which to transplant naked or encapsulated cells (Table II):

TABLE II

| BRAIN REGION | MEDIAL-LATERAL DIMENSION | DORSAL-VENTRAL DIMENSION | ANTERIOR-POSTERIOR DIMENSION |
|---|---|---|---|
| Gpe | 1.6 to 2.7 | 1.0 to −1.0 | 2.0 to −1.0 |
| Gpi | 0.5 to 2.0 | 0.5 to −0.7 | 0.7 to 2.0 |
| SNr | 0.5 to 1.5 | −0.6 to −1.5 | 0.7 to −0.7 |
| STN | 0.5 to 2.0 | 0.0 to −1.0 | 0.6 to −1.0 |
| NBM | 1.5 to 2.5 | 0.0 to −1.2 | 0.5 to 1.6 |
| Striatum: | 0.5 to 2.0 | 1.5 to 3.0 | 1.5 to 3.0 |
| caudate putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to said line; all dimensions are in centimeters; and Gpe means external segment of globus pallidus; Gpi means internal segment of globus pallidus; Snr means substantia nigra pars reticulata; STN means subthalamic nucleus; NBM means nucleus basalis of meynert; and caudate means caudate nucleus.

In particular for Parkinson's disease the transduction/transplantation site is selected from the group consisting of the substantia nigra pars reticulata (SNr) and the neostriatum.

Instead of in vivo transduction, nervous system diseases can be treated by transplanting to an individual in need thereof:
i. a therapeutically effective amount of the transduced or transfected cells according to the invention; or
ii. an implantable device comprising transduced or transfected cells.

Preferably, the transplantation comprises cells or implantable devices.

Said transplantation may comprise an autologous transplant, an allogeneic transplant or a xenogeneic transplant.

Target Tissues for Treatment of Neurodegenerative Disorders in the Central Nervous System An important parameter is the selection of a suitable target tissue. A region of the brain is selected for its retained responsiveness to neurotrophic factors. Targeting of an area may be achieved by delivering a dosage unit of a gene therapy vector as herein described or by implanting naked or encapsulated cells according to the invention.

In humans, CNS neurons which retain responsiveness to neurotrophic factors into adulthood include the cholinergic basal forebrain neurons, the entorhinal cortical neurons, the thalamic neurons, the locus coeruleus neurons, the spinal sensory neurons and the spinal motor neurons.

An initial scan, such as an MRI scan, may be performed on the patient to determine the precise location of the treatment site. For example, in treating Parkinson's disease, the basal ganglia, including substantia nigra, are treatment sites. The affected areas of the brain will likely of a size such that selection of 5 or fewer delivery sites will be sufficient for restoration of a clinically significant number of dopaminergic neurons. The same number of delivery sites may apply outside the brain.

For in vivo gene therapy, delivery may be systemic or local. By systemic delivery is intended administration of gene therapy vector intramuscularly, subcutaneously, or intraperiotoneally, which will result in continuous release of neublastin to the circulatory system.

For in vivo gene therapy, specific in vivo gene delivery sites are selected so as to cluster in an area of neuronal or terminal loss. Such areas may be identified clinically using a number of known techniques, including magnetic resonance imaging (MRI) and biopsy. In humans, non-invasive, in vivo imaging methods such as MRI will be preferred. Once areas of neuronal or terminal loss are identified, delivery sites are selected for stereotaxic distribution so each unit dosage of neublastin is delivered into the brain or spinal cord at, or within 500 μm from, a targeted cell, and no more than about 10 mm from another delivery site. Within the brain, gene therapy vector may be administered to the parenchyma or the ventricles.

Within the eye, gene therapy vector may be administered to the vitreous, the subretinal space and to the sub-tenar capsule.

For the treatment of peripheral neuropathy including neuropathic pain, the gene therapy vector may be administered to an area of the body involved in transmission of pain sensation. Such area may include the spinal cord and intrathecal administration.

Dosing Requirements and Delivery Protocol For in Vivo Gene Therapy

A further important parameter is the dosage of neublastin to be delivered into the target tissue. In this regard, "unit dosage" refers generally to the concentration of neublastin/ml of neublastin composition. For viral vectors, the neublastin concentration is defined by the number of viral particles/ml of neurotrophic composition. Optimally, for delivery of neublastin using a viral expression vector, each unit dosage of neublastin will comprise 2.5 to 25 μL of a neublastin composition, wherein the composition includes a viral expression vector in a pharmaceutically acceptable fluid and provides from $10^{10}$ up to $10^{15}$ neublastin containing viral particles per ml of neublastin composition. Such high titers are particularly used for adeno-associated virus. For lentivirus, the titer is normally lower, such as from $10^8$ to $10^{10}$ transducing units per ml (TU/ml), determined as described in Example 2.

The neublastin composition is delivered to each delivery cell site in the target tissue by microinjection, infusion, scrape loading, electroporation or other means suitable to directly deliver the composition directly into the delivery site tissue through a surgical incision. The delivery is accomplished slowly, such as over a period of about 5-10 minutes (depending on the total volume of neublastin composition to be delivered).

Those of skill in the art will appreciate that the direct delivery method employed by the invention obviates a limiting risk factor associated with in vivo gene therapy; to wit, the potential for transduction of non-targeted cells with the vector carrying the neublastin encoding transgene. In the invention, delivery is direct and the delivery sites are chosen so diffusion of secreted neublastin takes place over a controlled and pre-determined region of the brain to optimize contact with targeted neurons, while minimizing contact with non-targeted cells.

Gene Therapy Vectors

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells, which are then infused, grafted or otherwise transplanted into the patient. See, e.g., U.S. Pat. Nos. 4,868,116, 5,399,346 and 5,460,959. In vivo gene therapy seeks to directly target host patient tissue in vivo.

Viruses useful as gene transfer vectors include papovavirus, adenovirus, vaccinia virus, adeno-associated virus, herpesvirus, and retrovirus. Suitable retroviruses include the group consisting of HIV, SIV, FIV, EIAV, MoMLV.

Preferred viruses for treatment of disorders of the nervous system are lentiviruses and adeno-associated viruses. Both types of viruses can integrate into the genome without cell divisions, and both types have been tested in pre-clinical animal studies for indications of the nervous system, in particular the central nervous system.

Methods for preparation of AAV are described in the art, e.g. U.S. Pat. No. 5,677,158. U.S. Pat. No. 6,309,634 and U.S. Pat. No. 6,683,058 describe examples of delivery of AAV to the central nervous system.

Special and preferred types of retroviruses include the lentiviruses which can transduce a cell and integrate into its genome without cell division. Thus preferably the vector is a replication-defective lentivirus particle. Such a lentivivus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR. Methods for preparation and in vivo administration of lentivirus to neural cells are described in US 20020037281 (Methods for transducing neural cells using lentiviral vectors).

Retroviral vectors are the vectors most commonly used in human clinical trials, since they carry a 7-8 kb which is more than many other viral vectors and since they have the ability to infect cells and have their genetic material stably integrated into the host cell with high efficiency. See, e.g., WO 95/30761; WO 95/24929. Oncovirinae require at least one round of target cell proliferation for transfer and integration of exogenous nucleic acid sequences into the patient. Retroviral vectors integrate randomly into the patient's genome.

Two classes of retroviral particles have been described; ecotropic, which can infect mouse cells efficiently, and amphotropic, which can infect cells of many species. A third class includes xenotrophic retrovirus which can infect cells of another species than the species which produced the virus. Their ability to integrate only into the genome of dividing cells has made retroviruses attractive for marking cell lineages in developmental studies and for delivering therapeutic or suicide genes to cancers or tumors. These vectors may be particularly useful in the central nervous system, where there is a relative lack of cell division in adult patients.

For use in human patients, the retroviral vectors must be replication defective. This prevents further generation of infectious retroviral particles in the target tissue—instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7-8 kb.

Replication defective retroviral vectors require provision of the viral proteins necessary for replication and assembly in trans, from, e.g., engineered packaging cell lines. It is important that the packaging cells do not release replication competent virus and/or helper virus. This has been achieved by expressing viral proteins from RNAs lacking the $\psi$ signal, and expressing the gag/pol genes and the env gene from separate transcriptional units. In addition, in some packaging cell lines, the 5' LTR's have been replaced with non-viral promoters controlling expression of these genes and polyadenylation signals have been added. These designs minimize the possibility of recombination leading to production of replication competent vectors, or helper viruses. See, e.g., U.S. Pat. No. 4,861,719, herein incorporated by reference.

Expression Vectors

Construction of vectors for recombinant expression of neublastin for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982).

Briefly, construction of recombinant expression vectors employs standard ligation techniques. For analysis to confirm correct sequences in vectors constructed, the ligation mixtures may be used to transfect/transduce a host cell and successful genetically altered cells may be selected by antibiotic resistance where appropriate.

Vectors from the transfected/transduced cells are prepared, analysed by restriction and/or sequenced by, for example, the method of Messing, et al., (Nucleic Acids Res., 9: 309-,1981), the method of Maxam, et al., (Methods in Enzymology, 65: 499, 1980), the Sanger dideoxy-method or other suitable methods which will be known to those skilled in the art.

Size separation of cleaved fragments is performed using conventional gel electrophoresis as described, for example, by Maniatis, et al., (Molecular Cloning, pp. 133-134,1982).

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27: 299 (1981); Corden et al., Science 209: 1406 (1980); and Breathnach and Chambon, Ann. Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney mouse leukemia virus (MLV) and Rous sarcoma virus (RSV) LTRs contain promoter and enhancer sequences (Jolly et al., Nucleic Acids Res. 11: 1855 (1983); Capecchi et al., In : Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314: 285 (1985); Rossi and decrombrugghe, Proc. Natl. Acad. Sci. USA 84: 5590-5594 (1987)). Methods for maintaining and increasing expression of transgenes in quiescent cells include the use of promoters including collagen type I (1 and 2) (Prockop and Kivirikko, N. Eng. J. Med. 311: 376 (1984); Smith and Niles, Biochem. 19: 1820 (1980); de Wet et al., J. Biol. Chem., 258: 14385 (1983)), SV40 and LTR promoters.

According to one embodiment of the invention, the promoter is a constitutive promoter selected from the group consisting of: ubiquitin promoter, CMV promoter, JeT promoter, SV40 promoter, Elongation Factor 1 alpha promoter (EF1-alpha), chick beta-actin, PGK, MT-1 (Metallothionin).

Examples of inducible/repressible promoters include: Tet-On, Tet-Off, Rapamycin-inducible promoter, M×1, and RU486.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70 : 2702 (1973)). For example, in the present invention collagen enhancer sequences are used with the collagen promoter 2 (I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290: 304 (1981), and Fromm and Berg, J. Mol. Appl. Genetics, 1: 457 (1982), all of which are incorporated by reference herein. This repeat sequence can increase the transcription of many different viral and cellular genes when it is present in series with various promoters (Moreau et al., Nucleic Acids Res. 9 : 6047 (1981).

Transgene expression may also be increased for long term stable expression using cytokines to modulate promoter activity. Several cytokines have been reported to modulate the expression of transgene from collagen 2 (I) and LTR promoters (Chua et al., connective Tissue Res., 25: 161-170 (1990); Elias et al., Annals N. Y. Acad. Sci., 580 : 233-244 (1990)); Seliger et al., J. Immunol. 141: 2138-2144 (1988) and Seliger et al., J. Virology 62: 619-621 (1988)). For example, transforming growth factor (TOF), interleukin (IL)-I, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll (E)) can also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which down-regulates LTR promoter and Coll (E) promoter-enhancer, and reduces transgene expression.

The vector may comprise further sequences such as a sequence coding for the Cre-recombinase protein, and LoxP sequences. A further way of ensuring temporary expression of the neublastin is through the use of the Cre-LoxP system which results in the excision of part of the inserted DNA sequence either upon administration of Cre-recombinase to the cells (Daewoong et al, Nature Biotechnology 19:929-933) or by incorporating a gene coding for the recombinase into the virus construct (Plück, Int J Exp Path, 77:269-278). Incorporating a gene for the recombinase in the virus construct together with the LoxP sites and a structural gene (a neublastin in the present case) often results in expression of the structural gene for a period of approximately five days.

Pharmaceutical Preparations For Gene Therapy

To form a neublastin composition for use in the invention, neublastin encoding expression viral vectors may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of neublastin transgenes may be lyophilized using means well known in the art, for subsequent reconstitution and use according to the invention.

A colloidal dispersion system may also be used for targeted gene delivery.

Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6: 77,1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the neublastin at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6: 682,1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries.

Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further example of a delivery system includes transplantation into the therapeutic area of a composition of packaging cells capable of producing vector particles as described in the present invention. Methods for encapsulation and transplantation of such cells are known in the art, in particular from WO 97/44065 (Cytotherapeutics).

By selecting a packaging cell line capable of producing lentiviral particles, transduction of non-dividing cells in the therapeutic area is obtained. By using retroviral particles capable of transducing only dividing cells, transduction is restricted to de-novo differentiated cells in the therapeutic area.

Methods for Delivery of Gene Therapy Vector Composition

Following the protocol defined by the invention, direct delivery of a neublastin composition may be achieved by means familiar to those of skill in the art, including microinjection through a surgical incision (see, e. g., Capecchi, Cell, 22: 479-488 (1980)); electropotation (see, e. g., Andreason and Evans, Biotechniques, 6: 650-660 (1988)); infusion, chemical complexation with a targeting molecule or co-precipitant (e.g., liposome, calcium), and microparticle bombardment of the target tissue (Tang, et al., Nature, 356: 152-154 (1992)).

Encapsulation of Cells

Encapsulated cell therapy is based on the concept of isolating cells from the recipient host's immune system by surrounding the cells with a semipermeable biocompatible material before implantation within the host. The invention includes a device in which cells are encapsulated in an immunoisolatory capsule. An "immunoisolatory capsule" means that the capsule, upon implantation into a recipient host, minimizes the deleterious effects of the host's immune system on the cells in the core of the device. Cells are immunoisolated from the host by enclosing them within implantable polymeric capsules formed by a microporous membrane. This approach prevents the cell-to cell contact between host and implanted tissues, eliminating antigen recognition through direct presentation. The membranes used can also be tailored to control the diffusion of molecules, such as antibody and complement, based on their molecular weight (Lysaght et al., 56 J. Cell Biochem. 196 (1996), Colton, 14 Trends Biotechnol. 158 (1996)). Using encapsulation techniques, Cells can be transplanted into a host without immune rejection, either with or without use of immunosuppressive drugs. Useful biocompatible polymer capsules usually contain a core that contains cells, either suspended in a liquid medium or immobilized within an immobilizing matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semi-permeable nature of the capsule membrane also permits the biologically active molecule of interest to easily diffuse from the capsule into the surrounding host tissue.

The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by PCT International patent applications WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the genetically altered cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fiber structures can be used for cell implantation (U.S. Pat. No. 5,512,600, incorporated by reference). Biodegradable polymers include those comprised of poly(lactic acid) PLA, poly(lacticcoglycolic acid) PLGA, and poly(glycolic acid) PGA and their equivalents. Foam scaffolds have been used to provide surfaces onto which transplanted cells may adhere (PCT International patent application Ser. No. 98/05304, incorporated by reference). Woven mesh tubes have been used as vascular grafts (PCT International patent application WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. No. 4,976,859 or U.S. Pat. No. 4,968,733, incorporated by reference. An alternate surrounding semipermeable membrane material is poly(acrylonitrile/covinyl chloride).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

When macrocapsules are used, preferably between $10^3$ and $10^8$ cells are encapsulated, most preferably $10^5$ to $10^7$ cells are encapsulated in each device. Dosage may be controlled by implanting a fewer or greater number of capsules, preferably between 1 and 10 capsules per patient.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), intrathecal implantation, and the aqueous and vitreous humors of the eye (see, PCT International patent application WO 97/34586, incorporated by reference), the subretinal space, and the sub-tenar capsule. Within the brain, the devices may be implanted in the parenchyma and the ventricles. For systemic delivery, implantation may be intramuscular, subcutaneous, or intraperitoneal.

The ARPE-19 cell line is a superior platform cell line for encapsulated cell based delivery technology and is also useful for unencapsulated cell based delivery technology. The ARPE-19 cell line is hardy (i.e., the cell line is viable under stringent conditions, such as implantation in the central nervous system or the intra-ocular environment). ARPE-19 cells can be genetically modified to secrete a substance of therapeutic interest. ARPE-19 cells have a relatively long life span. ARPE-19 cells are of human origin. Furthermore, encapsulated ARPE-19 cells have good in vivo device viability. ARPE-19 cells can deliver an efficacious quantity of growth factor. ARPE-19 cells elicit a negligible host immune reaction. Moreover, ARPE-19 cells are non-tumorigenic.

Methods and apparatus for implantation of capsules into the CNS are described in U.S. Pat. No. 5,487,739.

In one aspect the invention relates to a biocompatible capsule comprising: a core comprising living packaging cells that secrete a viral vector for infection of a target cell, wherein the viral vector is a vector according to the invention; and an external jacket surrounding said core, said jacket comprising a permeable biocompatible material, said material having a porosity selected to permit passage of retroviral vectors of 100 nm diameter thereacross, permitting release of said viral vector from said capsule.

Preferably, the core additionally comprises a matrix, the packaging cells being immobilized by the matrix. According to one embodiment, the jacket comprises a hydrogel or thermoplastic material.

Examples of suitable cells for packaging cell lines include HEK293, NIH3T3, PG13, and ARPE-19 cells. Preferred cells include PG13 and 3T3 cells.

Methods and devices for encapsulation of packaging cells are disclosed in U.S. Pat. No. 6,027,721 hereby incorporated by reference in its entirety.

Host Cells

The nucleic acid constructs of the invention can be used to produce neublastin polypeptide. Eukaryotic cells may be transfected with a nucleic acid construct which encodes a recombinant neublastin polypeptide operatively linked to a heterologous signal sequence. Methods of making nucleic acid constructs and transfecting cells with the constructs are known in the art. (See e.g., Ausubel et al., eds., 1988, *Current Protocols in Molecular Biology*, Greene Publishing Associates & Wiley-Interscience: New York; Sambrook et al. 1989, *Molecular Cloning: A Laboratory Manual*, 2 ed., Cold Spring Harbor Laboratory Press: Cold Spring Harbor, N.Y.). In one aspect the invention relates to isolated host cells transduced or transfected with the vector according to the invention. These cells preferably are mammalian host cells because these are capable of secreting and processing the encoded neublastin correctly.

Preferred species include the group consisting of rodent (mouse, rat), rabbit, dog, cat, pig, monkey, human being.

Examples of primary cultures and cell lines that are good candidates for transduction with the vectors of the present invention include the group consisting of CHO, HEK293, COS, PC12, HiB5, RN33b, neuronal cells, foetal cells, RPE cell lines, ARPE-19, human immortalised fibroblasts, C2C12, HeLa, HepG2, striatal cells, neurons, astrocytes, interneurons.

One preferred type of cell line for encapsulation and for naked cell therapy are retinal pigment epithelial cells (RPE cells). The source of RPE cells is by primary cell isolation from the mammalian retina. Protocols for harvesting RPE cells are well-defined (Li and Turner, 1988, Exp. Eye Res. 47:911-917; Lopez et al., 1989, Invest. Ophthalmol. Vis. Sci. 30:586-588) and considered a routine methodology. In most of the published reports of RPE cell cotransplantation, cells are derived from the rat (Li and Turner, 1988; Lopez et al., 1989). Preferably, RPE cells are derived from humans. In addition to isolated primary RPE cells, cultured human RPE cell lines may be used in the practice of the invention.

For in vivo transduction, the preferred group of host cells includes striatal cells, neurons, astrocytes and interneurons. For ex vivo gene therapy, the preferred group of cells includes neuronal cells, neuronal precursor cells, neuronal progenitor cells, stem cells and foetal cells. Stem cells and neuronal precursor cells have the advantage that they can integrate into the tissue and migrate. For encapsulation and for implantation of naked cells the preferred cells include retinal pigmented epithelial cells, including ARPE-19 cells; human immortalised fibroblasts; and human immortalised astrocytes. Particularly preferred are ARPE-19

In another embodiment the therapeutic cell line is selected from the group consisting of: human fibroblast cell lines, human astrocyte cell lines, human mesencephalic cell lines, and human endothelial cell lines, preferably immortalised with TERT, SV40T or vmyc.

The method for generating an immortalised human astrocyte cell lines has previously been described (Price T N, Burke J F, Mayne L V. A novel human astrocyte cell line (A735) with astrocyte-specific neurotransmitter function. In Vitro Cell Dev Biol Anim. 1999 May;35(5):279-88.). This protocol may be used to generate astrocyte cell lines.

The following three modifications of that protocol are preferably made to generate additional human astrocyte cell lines.

Human foetal brain tissue dissected from 5-12 weeks old foetuses may be used instead of 12-16 weeks old tissue.

The immortalisation gene v-myc, or TERT (telomerase) may be used instead of the SV40 T antigen.

Retroviral gene transfer may be used instead of transfection with plasmids.

In Vitro Production of Neublastin

In a separate aspect the invention relates to mammalian cells, such as the cells defined above, capable of secreting neublastin or a functional equivalent thereof in amounts in excess of 500 ng/$10^6$ cells/24 hours, more preferably in excess of 600 ng/$10^6$ cells/24 hours, more preferably in excess of 700 ng/$10^6$ cells/24 hours, more preferably in excess of 800 ng/$10^6$ cells/24 hours, more preferably in excess of 900 ng/$10^6$ cells/24 hours, such as in excess of 1000 ng/$10^6$ cells/24 hours.

Preferably the secreted neublastin is biologically active as determined by the RetL3 ELISA assay described in Example 1. This obviates the need for glycosylation, cleavage and re-folding.

The preferred host cells are selected from the group consisting of CHO, HEK293 COS, PC12, HiB5, RN33b, C2C12, HeLa, HepG2, and ARPE-19 cells. More preferably the group consists of CHO, HEK293, COS, and ARPE-19.

Neublastin or a functional equivalent thereof can be produced by culturing these cells and recovering the neublastin from the culture medium without the need to refold or glycosylate the protein.

Expression can be increased even further by the inclusion of enhancer elements such as WPRE (U.S. Pat. No. 6,136,597).

Support Matrix for Neublastin Producing Cells

The present invention further comprises culturing neublastin producing cells in vitro on a support matrix prior to implantation into the mammalian nervous system. The preadhesion of cells to microcarriers prior to implantation is designed to enhance the long-term viability of the transplanted cells and provide long term functional benefit.

To increase the long term viability of the transplanted cells, i.e., transplanted neublastin secreting cells, the cells to be transplanted can be attached in vitro to a support matrix prior to transplantation. Materials of which the support matrix can be comprised include those materials to which cells adhere following in vitro incubation, and on which cells can grow, and which can be implanted into the mammalian body without producing a toxic reaction, or an inflammatory reaction which would destroy the implanted cells or otherwise interfere with their biological or therapeutic activity. Such materials may be synthetic or natural chemical substances, or substances having a biological origin.

The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amylases, natural and modified gelatin and natural and codified collagen, natural and modified polysaccharides, including dextrans and celluloses (e.g., nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of RPE cells. Thus, for example, the matrix material may be extracellular matrix or basement membrane material, which is produced and secreted by RPE cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors.

Alternatively, if the solid matrix to which the implanted cells are attached is constructed of porous material, the growth- or survival promoting factor or factors may be incorporated into the matrix material, from which they would be slowly released after implantation in vivo.

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead.

Bead sizes may range from about 10 µm to 1 mm in diameter, preferably from about 90 µm to about 150 µm. For a description of various microcarrier beads, see, for example, isher Biotech Source 87-88, Fisher Scientific Co., 1987, pp. 72-75; Sigma Cell Culture Catalog, Sigma Chemical Co., St, Louis, 1991, pp. 162-163; Ventrex Product Catalog, Ventrex Laboratories, 1989; these references are hereby incorporated by reference. The upper limit of the bead's size may be dictated by the bead's stimulation of undesired host reactions, which may interfere with the function of the transplanted cells or cause damage to the surrounding tissue. The upper limit of the bead's size may also be dictated by the method of administration. Such limitations are readily determinable by one of skill in the art.

EXAMPLES

Example 1

In Vitro Transfection with IgSP-NBN Construct

Construction of IgSP-NBN Constructs

IgSP.NBN was generated by overlap PCR. In the first amplification step, the mature fragment of NBN was amplified by PCR from the pUbilz.NBN.BamHI vector using the primers NBNs-IgSP.Flap (5'-GGTGAATTCG-GCTGGGGGCCCGGGCAGCC-3') (SEO ID NO: 38) and NBNas+XhoI(5'-TATACTCGAGCGAGCCC-TCAGC-CCAGGCA-3') (SEQ ID NO: 39). In a second PCR reaction, the IgSP sequence was amplified from the pNUT-IgSP-CNTF vector (ref. U.S. Pat. No. 6,361,741) using the primers IgSP-Kozakls+BamHI (5'-TATAGGATCCGCCACCATGAAAT-GCAGCTGGGT-TATC-3') (SEQ ID NO: 40) and IgSPas-NBN.Flap (5'-GGCCCCCAGCCGMTTCACCCCTGT-AGAAAG-3') (SEQ ID NO: 41). In the third step the products of step 1 and 2 were combined in a final PCR reaction that generates IgSP-NBN by using equal amounts of the two products as template with the primers IgSPKozakls+BamHI and NBN-as+XhoI.

Figure 3:
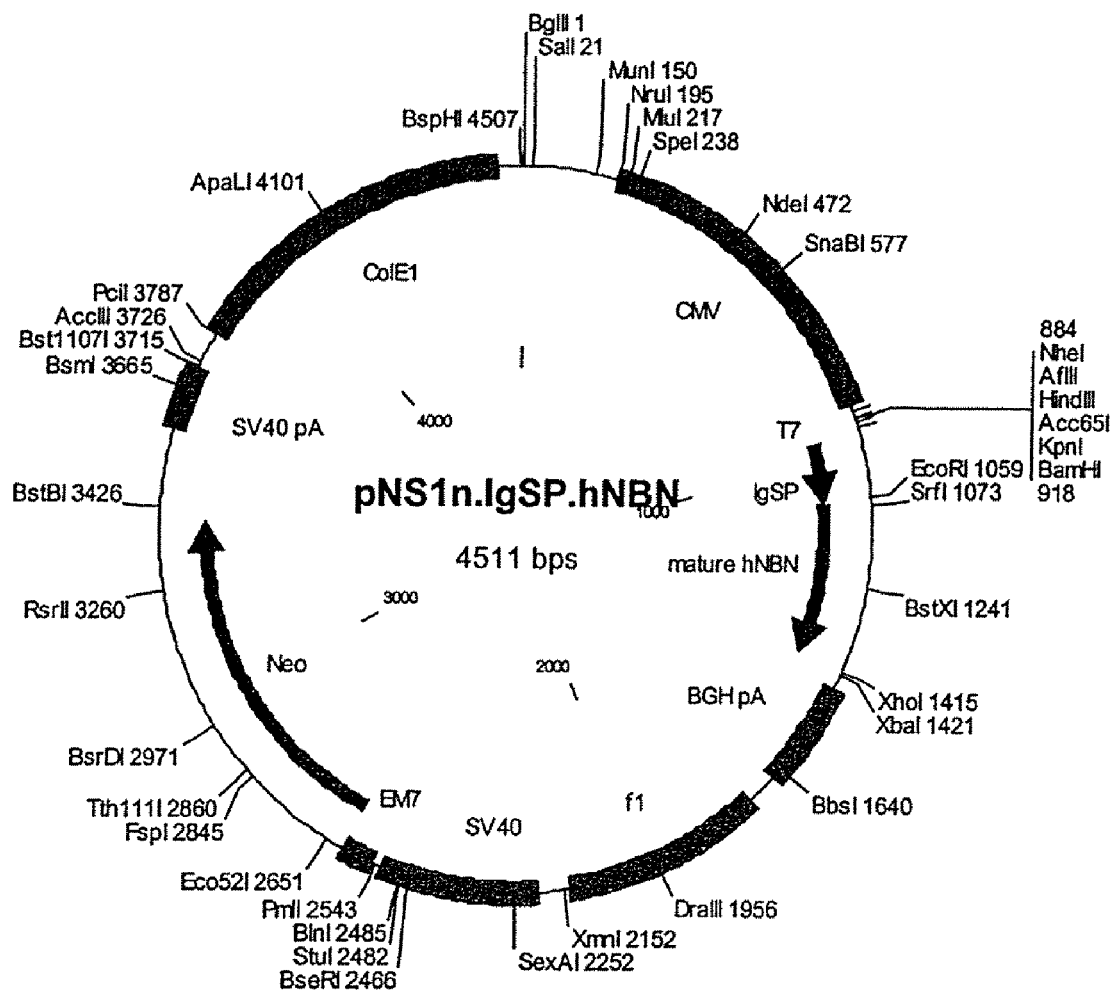
FIG. 3: Vector map of the pNS1n.IgSP.hNBN. Same IgSP-NBN sequence as pHsC.IgSP.hNBN.W between BamHI and XhoI restriction sites used in Example 1.

To generate a plasmid-based expression vector the resulting fragment was cloned in pNS1n digested with BamHI/XhoI. In this vector, the IgSP-NBN sequence is placed under transcriptional control of the CMV promoter (see FIG. 3). Furthermore, the vector contains the Neo gene that confers G418 resistance when expressed in mammalian cells.

Transient Transfection Studies

ARPE-19 is a human retinal pigment epithelial cell line (Dunn et al. 1996) grown in DMEM/Nutrient Mix F-12 with Glutamax (Invitrogen, Denmark) supplemented with 10% fetal bovine serum (Sigma-Aldrich, Denmark) at 37° C. and 5% $CO_2$. Cells were passaged approximately twice a week by trypsinization and reseeding (1:5 split ratio). Cells were seeded in 6-well plates (Corning Costar, Biotech Line, Denmark) at a density of $10^5$ cells/well for transfection studies. The next day, cells were transfected with 3 µg plasmid/well in duplicate wells using Fugene6 (Roche, Germany) according to the manufacturer's specifications. NBN activity present in cell supernatants collected 3 days after transfection was assayed in a RetL3 ELISA.

RetL3 ELISA

The RetL3 ELISA detects binding of a Ret-AP conjugate to a complex of NBN bound to the NBN-specific GFRα3 receptor. This assay will only detect NBN molecules which are functionally active. Briefly, a 96-well plate (B&W Isoplate HB, Perkin Elmer, Denmark) was coated with 100 µl 1 µg/ml Goat anti human Fc (Jackson Immunoresearch Laboratories, TriChem, Denmark) in 50 mM $NaHCO_3$ (pH=9.6) for 16 h at 4° C. After wash in PBS/0.05% Tween20 (PBST), wells were blocked in 0.2% I-Block (Tropix, Applied Biosystems, Denmark) in PBST for 1 hr at room temperature, followed by a brief wash in PBST. Cell supernatants or recombinant mouse Artemin (R&D systems, UK) were diluted in DMEM/10% FCS and subsequently incubated in the wells with 1 µg/ml GFRα3/Fc fusion protein (R&D Systems, UK) in RET-AP conditioned media (Biogen, USA) for 1.5 h at room temperature. Wells were then washed first in PBST and then in AP-buffer (200 mM Tris (pH=9.8), 10 mM $MgCl_2$) followed by 30 min incubation with 10% Sapphire Enhancer (Tropix, Applied Biosystems, Denmark) and 2% CSPD (Tropix, Applied Biosystems, Denmark) in AP-buffer. Luminescence was determined by using Microbeta Trilux Counter (Perkin Elmer, Denmark).

Figure 4:
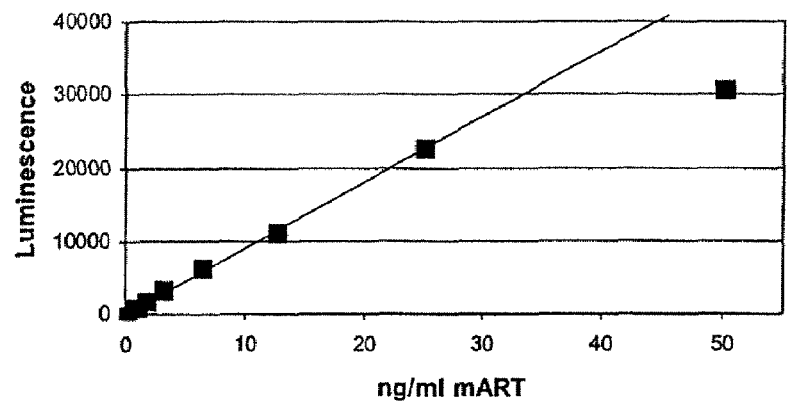
FIG. 4: Determination of NBN activity in the RetL3 ELISA (duplicate samples). (a) NBN activities in cell supernatants were determined using recombinant mouse Artemin produced in *E. coli* (mART) as standard, (b) Analysis of supernatants from transfected cells, (c) Analysis of supernatants from transduced cells.
Figure 4:
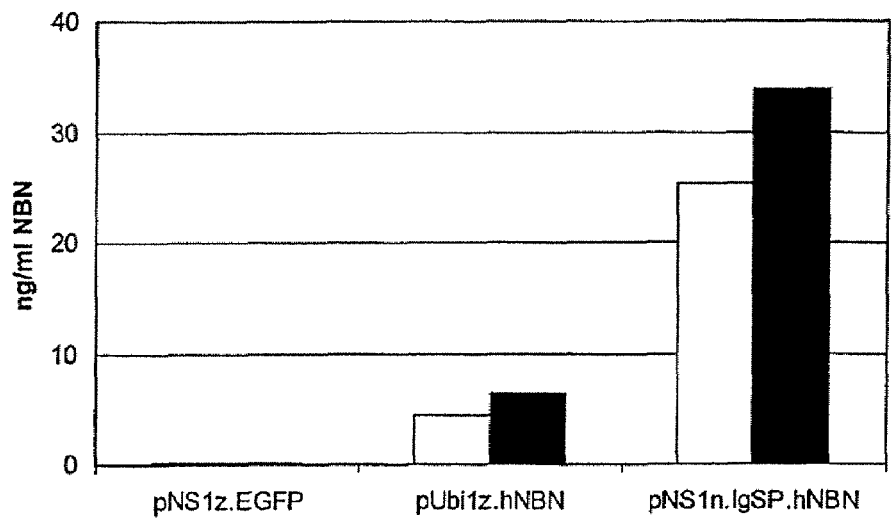
Figure 4:
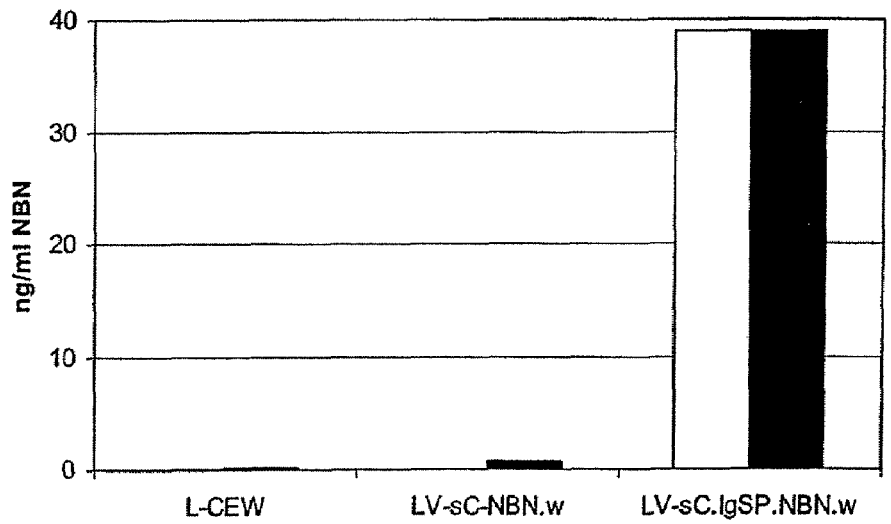
Figure 5:
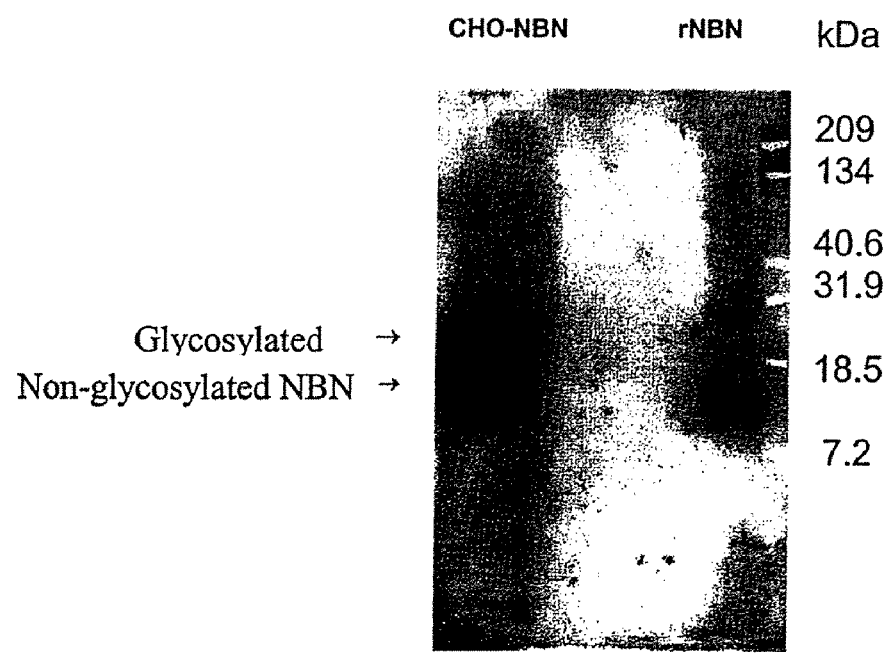
FIG. 5: Western blot analysis with the anti-NBN antibody #378. (a) Analysis of GFR[alpha]3 affinity purified NBN from CHO-NBN16 cells (CHO-NBN) and 20 ng rat recombinant NBN (rNBN) (b) Analysis of supernatants from ARPE-19 transfected or transduced with IgSP-NBN expression constructs and two CHO cell clones stably overexpressing NBN from a wildtype construct (CHO-NBN25c and CHO-NBN16). Arrows indicate the position of the glycosylated and non-glycosylated monomers of neublastin after reduction by the antibody #378.
Figure 5:
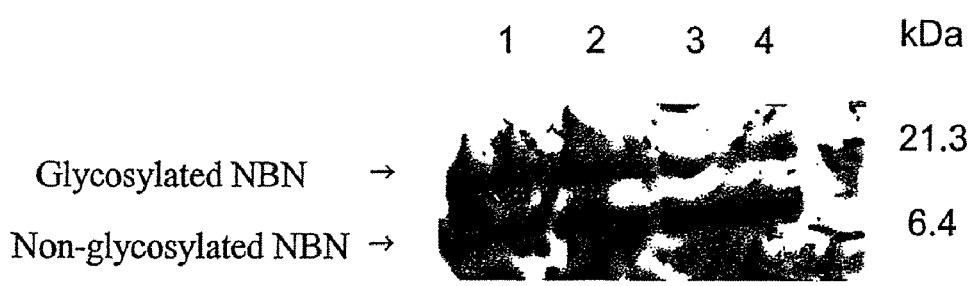

Results (FIG. 4, Panel (B))

NBN activities of 25.3-33.8 ng/ml were detected by using the RetL3 ELISA in supernatants collected from ARPE-19 cells transiently transfected with the pNS1n-Igsp.NBN construct. In contrast, approximately 5-fold lower NBN activity (4.4-6.4 ng/ml) is detected in ARPE-19 cells transiently transfected with a wild-type (prepro)NBN expression construct (pUbilz.hNBN) included in the same experiment. Very low or undetectable NBN activity was detected in cell supernatants of ARPE-19 transiently transfected with an EGFP expression construct (pNS1z-EGFP) confirming the specificity of the assay.

These results indicate that the use of a chimeric IgSP-NBN construct leads to higher release of mature NBN from mammalian cells capable of binding and activating the specific NBN receptor complex as compared to the release of NBN using a wildtype (prepro)NBN construct.

Example 2

In Vitro Transduction With IgSP-NBN Construct

Generation of a Lentiviral IgSP-NBN Construct and Virus Stocks

To generate a lentiviral construct, pNS1n-IgSP-NBN was digested with BamHI-XhoI and the IgSP-hNBN PCR fragment (as described in example 1) was ligated into BamHI/XhoI-digested pHsCXW resulting in pHsCXW.IgSP.NBNw (FIG. 3). pHsCXW is a derivative of a self-inactivating lentiviral transfer construct, pHR'-$SIN_{18}$ including a WPRE element (Dull et al., J.Virol., 72(11):8463-71(1998); Zufferey et al., J.Virol., 72(12):9873-80(1998): Zufferey et al. J.virol., 73 (4):2886-92 (1999)) generated by replacing the large non-viral part of the transfer construct with the pUC19 backbone. The sequence of pHsCXW can be accessed through GenGank ID: AY468486.

Replication-defective LV-sC.IgSP.NBN.W virus particles are generated by co-transfection of pHsC.IgSP.NBN.W with pMD.G (VSV-G pseudo-typing vector) and pBR8.91 (packaging vector) (Zufferey et al., Nat. Biotech., 15:871-75 (1997)) into 293T cells providing the required viral proteins in trans. Briefly, 293T cells cultured in DMEM with 4.5 g/l glucose and glutamax (Life Technologies, 32430-027) supplemented with 10% FCS (Life Technologies, 10099-141) are seeded in T75 flasks (2×106 cells/flask) the day before transfection. For each T75 flask cells are transfected with 5 µg pMD.G, 15 µg pBR8.91 and 20 µg of transfer vector using Lipofectamine+ following the manufacturer's instructions. Virus containing cell supernatant is collected 2-3 days after the transfection, filter-sterilized through a 0.45 m cellulose acetate or polysulphonic filter and concentrated by ultracentrifugation at 50,000×g for 90 min. at 4° C. After a second round of ultracentrifugation, the concentrated virus pellet is resuspended in DMEM, aliquoted and stored at −80° C. To determine virus titer, reverse transcriptase (RT) activity is assayed (Cepko and Pear, Current Protocols in Molecular Biology, 9.13.5-6, supplement 36) and transducing untis (TU)/ml calculated from the determined RT activity using an EGFP lentivirus with known transducing activity as reference.

Transduction Studies

ARPE-19 cells were transduced with NBN expression vectors. Briefly, cells were seeded in 6-well plates (Corning Costar, Biotech Line, Denmark) at a density of $10^5$ cells/well. The next day, $2\times10^5$ TU of virus was added pr. well (duplicates) together with 5 µg/ml polybrene for 4 h. The medium was changed and cultures were incubated for 3 days. Then cell supernatants were collected for RetL3 ELISA as described in Example 2.

Results (FIG. 4, Panel (C)).

NBN activities of 39 ng/ml were detected by using the RetL3 ELISA in supernatants collected from ARPE-19 cells transduced with the LV-sC.IgSP.NBN.W virus. In contrast, very low or undetectable NBN activity was detected in ARPE-19 cells transduced with a lenti-virus containing the wild-type (prepro)NBN cDNA (LV-sC-NBN.W) or a control EGFP lenti-virus (LV-sCEW).

These results indicate that, in contrast to a viral construct containing the wild type (prepro)NBN cDNA, the use of a chimeric IgSP-NBN viral construct allows high release of mature NBN from mammalian cells capable of binding and activating the specific NBN receptor complex.

Example 3

Analysis of NBN Protein Expressed from IgSP-NBN Constructs

Western Blot Analysis of Cell Supernatants

NBN present in cell supernatants from transfected or transduced cell cultures was concentrated by affinity binding to GFRα3-Ig prior to Western blot analysis. Briefly, 4 wells of a Nunc MaxiSorp plate were coated with 300 μl Goat anti human Fc 1 μg/ml (Jackson Immunoresearch Laboratories, TriChem, Denmark) in 50 mM $NaHCO_3$ (pH=9.6) for 16 h at 4° C. The wells were blocked with 400 μl 1% BSA in PBS for 1 h at room temperature, followed by 3 washes in PBST. 300 μl/well GFRα3/Fc fusion protein 1 μg/ml (R&D Systems, UK) was then added and the plate was incubated for 1 h at room temperature to maximise binding. The wells were then emptied and washed again 3 times with PBST. 300 μl supernatant collected from transfected or transduced cell cultures was then added to each of the 4 wells and incubated for at least 3 h with gently shaking at room temperature. The wells were then washed twice in PBST. 20 μl of non-reducing sample buffer (2% SDS, 0.4 M Tris (ph=8.0) was added to the first well and the plate shaken rapidly for 5 min. to elute the bound proteins. The content was transferred to the next well and the procedure was repeated to elute the proteins bound in the remaining wells. After addition of DTT to 10 mM, the samples were heated to 96° C. for 5 minutes and analysed by SDS PAGE on a 15% polyacrylamide gel using the MultiPhor II system according to the manufacturer's recommendations (Amersham Pharmacia, Denmark). The proteins were the blotted to PVDF membranes (BioRad, Denmark) that was immunostained using a rabbit polyclonal anti-NBN antibody (#378) as detecting antibody. Membranes were developed using the ECL+ system (Amersham Pharmacia, Denmark) and subjected to film exposure.

Results

The #378 is a rabbit polyclonal antibody raised against an NBN-derived peptide (ALRPPPGSRPVSQPC) (SEQ ID NO: 45). As seen in FIG. 5 panel (a) a single band of a molecular weight between 7.2 and 18.5 kDa is recognized in reduced (+DTT) samples containing purified rat recombinant NBN produced in *E. coli* corresponding to the monomeric unglycosylated NBN113. A band of the same MW in addition to several additional bands are recognized in reduced samples from stable CHO-NBN clones established by transfection with wt(prepro)NBN. The identities of a number of these bands have been determined in previous studies using deglycosylation and N-terminal sequencing. A band with slightly lower molecular weight represents a smaller and unglycosylated version of mature NBN (NBN104). In addition a very broad band with an apparent MW of approximately 21 kDa represent glycosylated versions of NBN113 and NBN104. Bands of higher MW represent (glycosylated) pro-NBN seen occasionally in GFR.alpha.3-affinity purified samples.

As seen in FIG. 5 panel b, the double band of MW between 6.4 and 21.3 kDa corresponding to unglycosylated NBN113 and NBN104 is detected in two stable clones of CHO-NBN cells. The same double band is also detected in ARPE-19 transduced or transfected with IgSP-NBN expression constructs. Furthermore, a double band of MW close to 21 kDa corresponding to glycosylated NBN113 and NBN104 is seen in all samples analysed. These results indicate that processing and posttranslational modification are similar when expressed from wt(prepro)NBN and IgSP-NBN constructs.

Example 4

Sequences of Chimeric IgSP-NBN Viral Construct and Prediction of Signal Peptide IgSP-NBN—Nucleotide Sequence Present in Construct

```
ATGAAATGCAGCTGGGTTATCTTCTTCCTGATGGCAGTGGTTACAGGTAAGGGGCTCCCA  (SEQ ID NO 7)
AGTCCCAAACTTGAGGGTCCATAAACTCTGTGACAGTGGCAATCACTTTGCCTTTCTTTC
TACAGGGGTGAATTCGGCTGGGGGCCCGGGCAGCCGCGCTCGGGCAGCGGGGGCGCGGGG
CTGCCGCCTGCGCTCGCAGCTGGTGCCGGTGCGCGCGCTCGGCCTGGGCCACCGCTCCGA
CGAGCTGGTGCGTTTCCGCTTCTGCAGCGGCTCCTGCCGCCGCGCGCGCTCTCCACACGA
CCTCAGCCTGGCCAGCCTACTGGGCGCCGGGGCCCTGCGACCGCCCCCGGGCTCCCGGCC
CGTCAGCCAGCCCTGCTGCCGACCCACGCGCTACGAAGCGGTCTCCTTCATGGACGTCAA
CAGCACCTGGAGAACCGTGGACCGCCTCTCCGCCACCGCCTGCGGCTGCCTGGGCTGA
```

IgSP-NBN is a fusion construct with the signal peptide from an immunoglobulin gene fused directly to mature NBN (113).

The IgSP-NBN Contains an Intron

Intron-exon prediction by NetGene (CBS-DTU server):

```
Length: 478 nucleotides.

13.4% A, 36.2% C, 32.2% G, 18.2% T, 0.0% X, 68.4% G + C

Donor splice sites, direct strand pos 5' -> 3' phase  strand confidence  5' exon intron
3'
    47            2       +      0.00        GTGGTTACAG
                                             ^GTAAGGGGCT
    248           0       +      0.60        CGACGAGCTG
                                             ^GTGCGTTTCC Donor splice sites, complement strand No donor site predictions above threshold.

Acceptor splice sites, direct strand pos 5' -> 3' phase  strand confidence  5' intron exon
3'
    125           1       +      0.83        CTTTCTACAG
                                             ^GGGTGAATTC
    153           2       +      0.18        GCCCGGGCAG
                                             ^CCGCGCTCGG
    167           1       +      0.20        GCTCGGGCAG
                                             ^CGGGGGCGCG
    199           0       +      0.42        GCGCTCGCAG
                                             ^CTGGTGCCGG Nucleotide sequence of spliced transcript:
ATGAAATGCAGCTGGGTTATCTTCTTCCTGATGGCAGTGGTTACAGGGGTGAATTCGGCT    (SEQ ID NO 8)
GGGGGCCCGGGCAGCCGCGCTCGGGCAGCGGGGGCGCGGGGCTGCCGCCTGCGCTCGCAG
CTGGTGCCGGTGCGCGCGCTCGGCCTGGGCCACCGCTCCGACGAGCTGGTGCGTTTCCGC
TTCTGCAGCGGCTCCTGCCGCCGCGCGCGCTCTCCACACGACCTCAGCCTGGCCAGCCTA
CTGGGCGCCGGGGCCCTGCGACCGCCCCCGGGCTCCCGGCCCGTCAGCCAGCCCTGCTGC
CGACCCACGCGCTACGAAGCGGTCTCCTTCATGGACGTCAACAGCACCTGGAGAACCGTG
GACCGCCTCTCCGCCACCGCCTGCGGCTGCCTGGGCTGA Translation of spliced transcript:
MKCSWVIFFLMAVVTGVNSAGGPGSRARAAGARGCRLRSQLVPVRALGLGHRSDELVRFR    (SEQ ID NO 9)
FCSGSCRRARSPHDLSLASLLGAGALRPPPGSRPVSQPCCRPTRYEAVSFMDVNSTWRTV
DRLSATACGCLG
```

The translated fusion protein is predicted to contain a 19 amino acid signal peptide, which is cleaved from the mature NBN (113) sequence using Signal P (available at the CBS DTU server). (Identification of prokaryotic and eukaryotic peptides and prediction of their cleavage sites. H. Nielsen, J. Engelbrecht, S. Brunak, G. von Hejne, Protein Engineering 10, 1-6, 1997.)

Figure 6A:
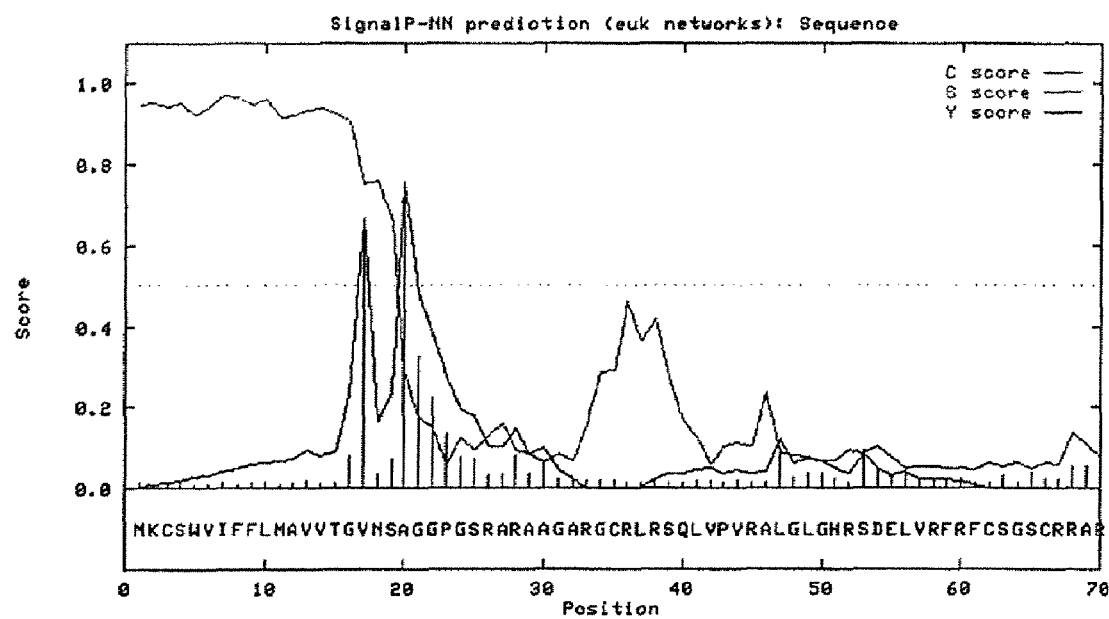
FIGS. 6A and 6B. Prediction of signal peptide cleavage by SignalP. For explanation see Example 4.

SignalP-NN Result (See FIG. 6a):

| # Measure | Position | Value | Cutoff | signal peptide? |
|---|---|---|---|---|
| | >Sequence length = 70 | | | |
| max. C | 20 | 0.757 | 0.33 | YES |
| max. Y | 20 | 0.758 | 0.32 | YES |
| max. S | 7 | 0.970 | 0.82 | YES |
| mean S | 1-19 | 0.906 | 0.47 | YES |

Most likely cleavage site between pos. 19 and 20: VNS-AG

Figure 6B:
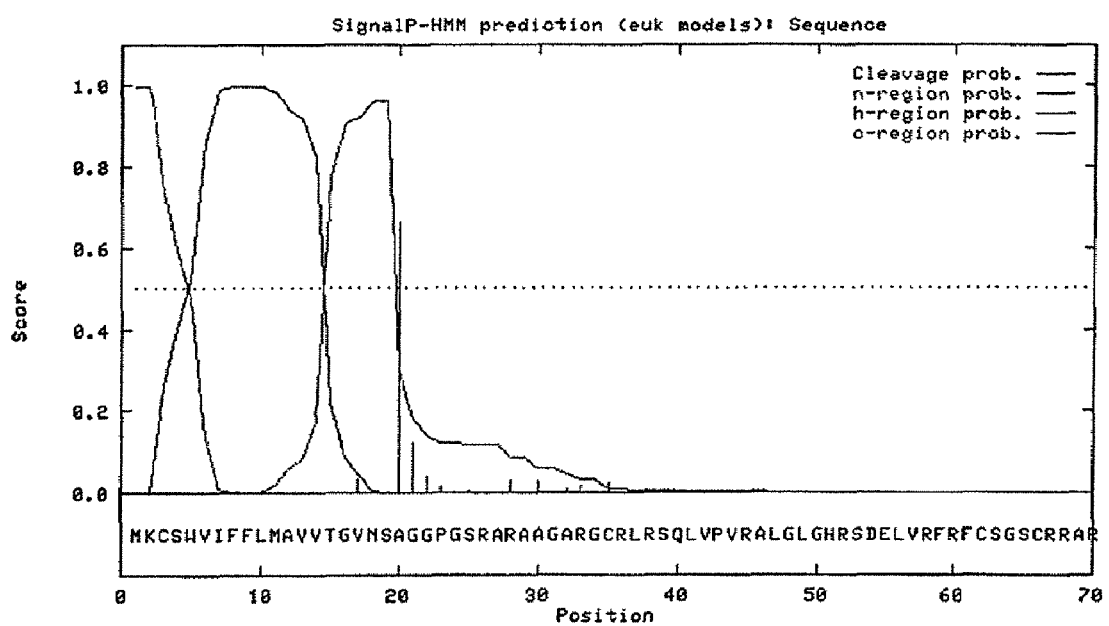

SignalP-HMM Result (See FIG. 6b):

Prediction: Signal peptide

Signal peptide probability: 0.999

Signal anchor probability: 0.000

Max cleavage site probability: 0.660 between pos. 19 and 20

Using neural networks (NN) and hidden Markov models (HMM) trained on eukaryotes

Example 5

Prediction of Positions for Signal Peptides

The prediction of cleavage site when Igsp is fused to a neublastin polypeptide of various length is shown below using the signal P programme 2.0 identified above.

```
Cleavage sites:

Protein       SignalP-NN       SignalP-HMM     Remarks

Pre-pro-NBN 39/40 *            39/40 (0,348)   Very long signal
            (0,852)                            peptide with low
                                               probability in N-
                                               terminus IgSP-NBN113 19/20 (0,757)      19/20 (0,660)

IgSP-NBN106 19/20 (0,831)      22/23 (0,586)   19/20 cleavage
                                               predicted with less
                                               probability in HMM
                                               (0,2)

IgSP-NBN104 19/20 (0,643)      22/23 (0,440)   19/20 cleavage
                                               predicted with less
                                               probability in HMM
                                               (0,18).
                                               Furthermore, an
                                               additional cleavage
                                               site 25/26 is
                                               predicted with
                                               same probablity IgSP-NBN102 16/17 (0,643)      19/20 (0,359)   19/20 cleavage
                                               predicted with a
                                               probability of 0,5 by
                                               NN IgSP-NBN99  19/20 (0,718)      19/20 (0,496)

IgSP:
(19)MKCSWVIFFLMAVVTGVNS
Mature forms of NBN:
(113)AGGPGSR(106)AR(104)AA(102)GAR(99)GCRLRSQLVPVRALGLGHRS-
DELV
RFRFCSGSCRRARSPHDLSLASLLGAGALRPPPGSRPVSQPCCRPTRYEAVSFMD
VNSTWRTVDRLSATACGCLG
```

Example 6

Cloning of Deltapro-NBN into pHsCXW

Deltapro-NBN (SEQ. ID. NO: 37) was generated by overlap PCR in three amplification steps: 1) The relatively long 117 bp leader sequence (i.e. 39 a.a. signal peptide) of pre-proNBN with 5' BamHI/Kozak overhang and 10 base 3' overlap to mature NBN (143 bp); 2) mature NBN with 5' 10 base NBN leader sequence overlap and 3' XhoI (362 bp); 3) the products of steps 1 and 2 were combined in a final PCR reaction that generated Δpro-NBN (492 bp).

The first PCR reaction (NBN leader):
Primers used:

```
BamHI + Kozak + hNBNsp,
5'-TATAGGATCCGCCACCATGGAACTTGGACTTGGAGG-3'
(SEQ ID NO: 42)

hNBNsp3'-matNBN FLAP as,
5'-GGCCCCCAGCGGCCTCTGCGACGCTGCTCA-3'
(SEQ ID NO: 43).
```

Figure 7A:
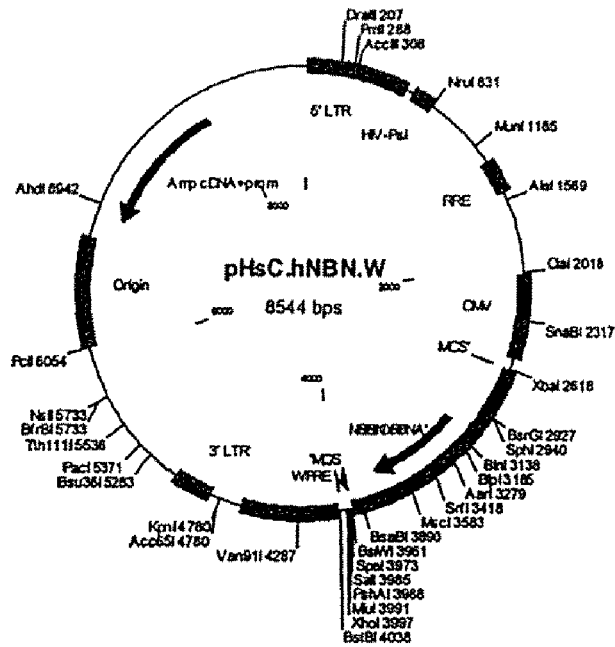
FIG. 7A shows plasmid pHs C.hNBN.W

Plasmid pHsC.hNBN.W (see plasmid map in FIG. 7a) was used as template for the PCR reaction, which was run using Pfu-turbo polymerase.

| PCR conditions: | |  |
|---|---|---|
| 94° C. | 3 min | |
| 94° C. | 30 s | |
| 55° C. | 30 s | 35 cycles |
| 72° C. | 1 min | |
| 72° C. | 5 min | |

The second PCR reaction (matureNBN):
Primers used:

```
hNBNsp3' FLAP-matNBN s,
5'-CGCAGAGGCCGCTGGGGGCCCGGGCAGC-3'
(SEQ ID NO: 43) and NBNas + XhoI,
5'-TATACTCGAGCGAGCCCTCAGCCCAGGCA-3'
(SEQ ID NO: 39).
```

Plasmid pHsC.hNBN.W (see plasmid map FIG. 7a) was used as template for the PCR reaction, which was run using Pfu-turbo polymerase.

| PCR conditions: | |
|---|---|
| 94° C. | 3 min |
| 94° C. | 30 s |

-continued

PCR conditions:

| 65° C. | 30 s | 35 cycles |
| 72° C. | 1 min | |
| 72° C. | 5 min | |

The third PCR reaction (deltapro-NBN):

```
Primers used:

BamHI + Kozak + hNBNsp,
5'-TATAGGATCCGCCACCATGGAACTTGGACTTGGAGG-3'
SEQ ID NO: 44) and NBNas + XhoI,
5'-TATACTCGAGCGAGCCCTCAGCCCAGGCA-3'
(SEQ ID NO: 39).
```

The PCR fragments from the two first PCR reactions (NBN leader and mature NBN both at a 1:10 dilution) were used as template for the third PCR reaction, which was run using Pfu-turbo polymerase, and the same PCR profile as the first PCR run.

Figure 7B:
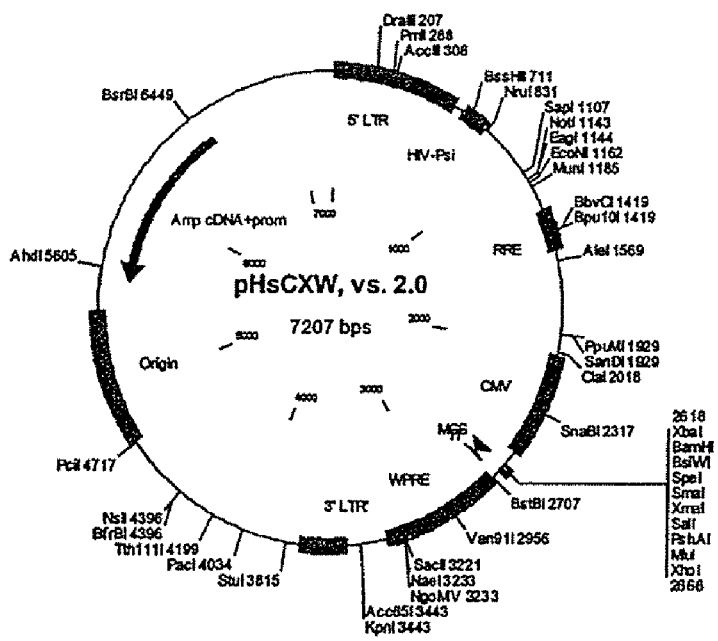
FIG. 7B shows plasmid pHsCXW. For explanation see Example 6.

The PCR fragment from the third PCR reaction was cut with BamHI and XhoI and cloned between BamHI and XhoI sites in pHsCXW (see plasmid map in FIG. 7b).

Example 7

In Vitro Transfection With IgSP-NBN and DeltaproNBN Construct in Different Cell Lines Secretion of NBN after transient transfection with different NBN constructs, including wt pre-pro NBN, delta-pro NBN and IgSP-NBN were compared. Transient transfections were performed in ARPE-19, HEK293, CHO and HiB5 cells.

Cell Lines

ARPE-19 cells were cultured as described in example 1. HiB5 (Renfranz et al. 1991), HEK293 and CHO cells were grown in DMEM (Invitrogen, Denmark) with 10% fetal bovine serum (Invitrogen, Denmark), and medium for CHO cells were further supplemented with 20 mg/l L-proline. ARPE-19, HEK293 and CHO cells were grown at 37° C. and HiB5 cells at 33° C. in 5% $CO_2$. Cells were passaged approximately twice a week by trypsinization and reseeding (1:5 split ratio).

NBN Secretion After Transient Transfection

Cells were seeded in 6-well plates (Corning Costar, Biotech Line, Denmark) at a density of approximately $10^5$ cells/well. The next day, cells were transfected with pHsC.hN-BN.W, pHsC.IgSP.hNBN.W and pHsC.deltapro-hNBN.W, respectively. ARPE-19 cells were transfected in triplicate wells using Fugene6 as described in example 1, whereas the other three cell lines were transfected using 2 μg plasmid/well in triplicate wells using Lipofectamine Plus (Invitrogen, Denmark) according to the manufacturer's instructions. The next day, fresh growth medium was added to the wells, and cells were incubated for further 24 hours before collecting conditioned medium. Sufficient transfection efficiency was ensured by evaluation of EGFP expression in wells transfected in parallel with pHsC.EGFP.W. NBN binding activity in conditioned medium was measured using the RetL3 ELISA, as described in example 1. The RetL3 ELISA detects binding of a Ret-AP conjugate to a complex of NBN bound to the NBN-specific GFRα3 receptor. Values were calculated as ng NBN/ml/24 h and ng NBN/$10^5$ cells/24 h and adjusted to relative NBN release with values from cells transfected with the wt NBN construct set to 1. Data in FIG. 8 represent these three calculations and are expressed as mean ± SEM (n=3). In panel A, * indicates a significant difference from cells transfected with the wt NBN construct (P<0.05, one way ANOVA, Fisher LSD Method)

Results

Figure 8A:
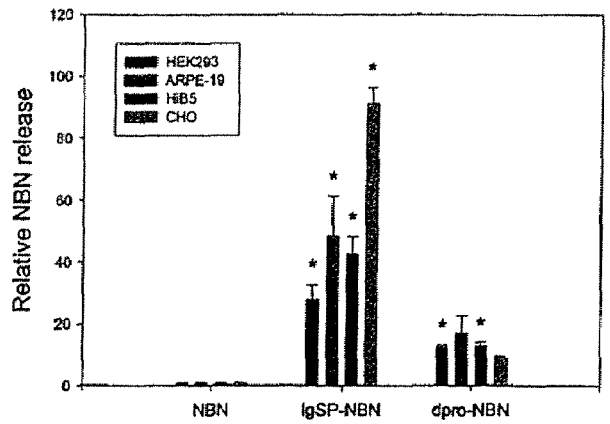
FIG. 8A shows relatives NBN release conditioned medium and FIGS. 8B and 8C show NBN in different cell lines, see also Example 7.

As shown in the table below and FIG. 8A, the four tested cell lines showed increased NBN release when using the deltapro-NBN construct, compared to the wt NBN construct (9-17 fold higher NBN release, depending on cell line). When transfecting the four cell lines with the pHsC.IgSP.hNBN construct, NBN secretion was further enhanced (28-91 fold higher NBN release compared to wt NBN). Very low or undetectable NBN activity was seen in cell supernatants from ARPE-19 transiently transfected with the EGFP expression construct (pHs.C.EGFP.W) confirming the specificity of the assay.

| Construct | HEK293 Mean | S.E.M. | ARPE-19 Mean | S.E.M. | HiB5 Mean | S.E.M. | CHO Mean | S.E.M. |
|---|---|---|---|---|---|---|---|---|
| NBN | 1.0 | 0.2 | 1.0 | 0.3 | 1.0 | 0.2 | 1.0 | 0.1 |
| IgSP-NBN | 28.0 | 4.7 | 48.6 | 12.9 | 42.7 | 5.4 | 91.2 | 5.1 |
| dpro-NBN | 12.4 | 0.6 | 17.2 | 5.5 | 13.1 | 1.0 | 9.2 | 25.5 |

Figure 8B:
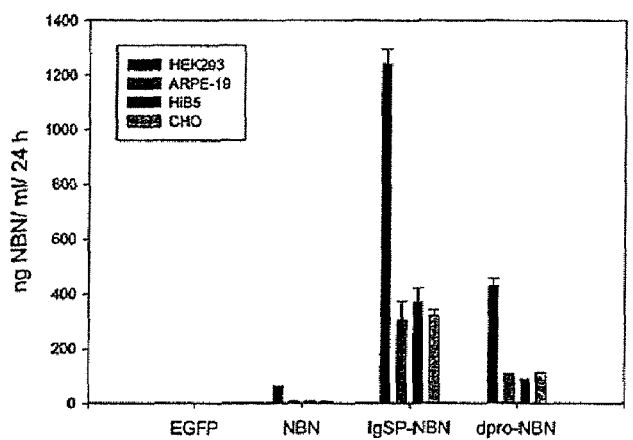
Figure 8C:
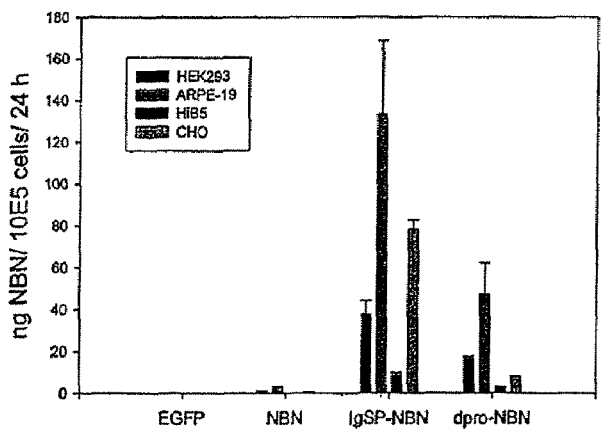

Panel B in FIG. 8B shows NBN concentrations in conditioned medium (24 h) from the transiently transfected cell lines. The highest concentration (1240±54 ng NBN/ml) was found in conditioned medium from HEK293 cells transfected with the IgSP-NBN construct. Panel C in FIG. 8C shows NBN release per $10^5$ cells per 24 h. IgSP-NBN transfected ARPE-19 cells showed the highest NBN release (133±35 ng/$10^5$ cells/24 h).

The present results indicate that the use of a chimeric IgSP-NBN construct and of deltapro NBN construct in order to increase secretion of mature NBN from mammalian cells is applicable in different cell types.

Example 8

Prediction Using SignalP 3.0

Prediction of positions for signal peptides using version 3.0. The predictions were carried out on deltapro NBNs and IgSP-NBNs of the following sequences.

Chimeric NBN molecules with NBN-SP (deltapro NBNs):

NBN-SP (SEQ ID NO: 24)
MELGLGGLSTLSHCPWPRRQPALWPTLAALALLSSVAIEA deltaproNBN140 (SEQ ID NO: 25)
MELGLGGLSTLSHCPWPRRQPALWPTLAALLSSVAEAPPPQPSRPAPPPPAPPSALP-
RGGRAARAGGPGSRARAAGARGCRLRSQLVPVRALGLGHRSDELVRFRFCSGSCRRAR-
SPHDLSLASLLGAGALRPPPGSRPVSQPCCRPTRYEAVSFMDVNSTWRTVDRLSATACG-
CLG deltaproNBN113 (SEQ ID NO: 26)
MELGLGGLSTLSHCPWPRRQPALWPTLAALALLSSVAEAAGGPGSRARAAGARGCRLRS-
QLVPVRALGLGHRSDELVRFRFCSGSCRRARSPHDLSLASLLGAGALRPPPGSRPVSQP-
CCRPTRYEAVSFMDVNSTWRTVDRLSATACGCLG deltaproNBN106 (SEQ ID NO: 27)
MELGLGGLSTLSHCPWPRRQPALWPTLAALALLSSVAEAARAAGARGCRLRSQLVPVRA-
LGLGHRSDELVRFRFCSGSCRRARSPHDLSLASLLGAGALRPPPGSRPVSQPCCRPTRY-
EAVSFMDVNSTWRTVDRLSATACGCLG deltaproNBN104 (SEQ ID NO: 28)
MELGLGGLSTLSHCPWPRRQPALWPTLAALALLSSVAEAAAGARGCRLRSQLVPVRALG-
LGHRSDELVRFRFCSGSCRRARSPHDLSLASLLGAGALRPPPGSRPVSQPCCRPTRYEA-
VSFMDVNSTWRTVDRLSATACGCLG deltaproNBN102 (SEQ ID NO: 29)
MELGLGGLSTLSHCPWPRRQPALWPTLAALALLSSVAEAGARGCRLRSQLVPVRALGLG-
HRSDELVRFRFCSGSCRRARSPHDLSLASLLGAGALRPPPGSRPVSQPCCRPTRYEAVS-
FMDVNSTWRTVDRLSATACGCLG deltaproNBN99 ((SEQ ID NO: 30)
MELGLGGLSTLSHCPWPRRQPALWPTLAALALLSSVAEAGCRLRSQLVPVRALGLGHRS-
DELVRFRFCSGSCRRARSPHDLSLASLLGAGALRPPPGSRPVSQPCCRPTRYEAVSFMD-
VNSTWRTVDRLSATACGCLG Chimeric NBN molecules with IgSP (IgSP-NBNs)

IgSP (SEQ ID NO: 4)
MKCSWVIFFLMAVVTGVNS

IgSP-NBN140 (SEQ ID NO: 31)
MKCSWVIFFLMAVVTTGVNSPPPQPSRPAPPPPAPPSALPRGGRAARAGGPGSRARAAGA-
RGCRLRSQLVPVRALGLGHRSDELVRFRFCSGSCRRARSPHDLSLASLLGAGALRPPPGS-
RPVSQPCCRPTRYEAVSFMDVNSTWRTVDRLSATACGCLG

IgSP-NBN113 ((SEQ ID NO: 32)
MKCSWVIFFLMAVVTGVNSAGGPGSRARAAGARGCRLRSQLVPVRALGLGHRSDELVR-
FRFCSGSCRRARSPHDLSLASLLGAGALRPPPGSRPVSQPCCRPTRYEAVSFMDVNST-
WRTVDRLSATACGCLG

IgSP-NBN106 (SEQ ID NO: 33)
MKCSWVIFFLMAVVTGVNSARAAGARGCRLRSQLVPVRALGLGHRSDELVRFRFCSGSC-
RRARSPHDLSLASLLGAGALRPPPGSRPVSQPCCRPTRYEAVSFMDVNSTWRTVDRLSA-
TACGCLG

IgSP-NBN104 (SEQ ID NO: 34)
MKCSWVIFFLMAVVTGVNSAAGARGCRLRSQLVPVRALGLGHRSDELVRFRFCSGSCRR-
ARSPHDLSLASLLGAGALRPPPGSRPVSQPCCRPTRYEAVSFMDVNSTWRTVDRLSATA-
CGCLG

IgSP-NBN102 (SEQ ID NO: 35)
MKCSWVIFFLMAVVTGVNSGARGCRLRSQLVPVRALGLGHRSDELVRFRFCSGSCRRAR-
SPHDLSLASLLGAGALRPPPGSRPVSQPCCRPTRYEAVSFMDVNSTWRTVDRLSATACG-
CLG

IgSP-NBN99 (SEQ ID NO: 36)
MKCSWVIFFLMAVVTGVNSGCRLRSQLVPVRALGLGHRSDELVRFRFCSGSCRRARSPH-
DLSLASLLGAGALRPPPGSRPVSQPCCRPTRYEAVSFMDVNSTWRTVDRLSATACGCLG

The signal peptide predictions are shown below in the tables:

Signal peptide predictions for proteins with NBN signal peptide[1] (deltapro)

| Protein | Signal P 3.0 - NN | | | | SignalP - HMM | | | Remarks |
|---|---|---|---|---|---|---|---|---|
| | Mean S | D | Max. C | Cleavage site | SP probability | Cleavage site probability | Cleavage site | |
| Prepro-NBN | 0.5 | 0.551 | 0.451 | 39/40 | 0.993 | 0.573 | 39/40 | |
| deltaproNBN140 | 0.437 | 0.569 | 0.711 | 39/40 | 0.993 | 0.845 | 39/40 | |
| deltaproNBN113 | 0.492 | 0.616 | 0.693 | 39/40 | 0.998 | 0.675 | 39/40 | |
| deltaproNBN106 | 0.505 | 0.564 | 0.495 | 39/40 | 0.998 | 0.415 | 39/40 | |
| deltaproNBN104 | 0.509 | 0.500 | 0.305* | (39/40) | 0.998 | 0.278* | (39/40) | |
| deltaproNBN102 | 0.492 | 0.508 | 0.352 | 39/40 | 0.996 | 0.514 | 39/40 | |
| DeltaproNBN99 | 0.497 | 0.555 | 0.478 | 39/40 | 0.991 | 0.724 | 39/40 | |
| Cuttoff values | 0.48 | 0.43 | 0.32 | | 0.5 | | | |

[1]MELGLGGLSTLSHCPWPRRQPALWPTLAALALLSSVAEA- 39 amino acids
*Below cuttoff values Signal peptide predictions for proteins with IgSP[2]

| Protein | Signal P 3.0 - NN | | | | SignalP - HMM | | | Remarks |
|---|---|---|---|---|---|---|---|---|
| | Mean S | D | Max C | Cleavage site | SP probability | Cleavage site probability | Cleavage site | |
| IgSP-NBN140 | 0.853 | 0.844 | 0.906 | 19/20 | 0.999 | 0.823 | 19/20 | |
| IgSP-NBN113 | 0.927 | 0.893 | 0.901 | 19/20 | 1.000 | 0.877 | 19/20 | |
| IgSP-NBN106 | 0.935 | 0.847 | 0.803 | 19/20 | 1.000 | 0.557 | 22/23 | Cleavage site at 19/20 predicted with lower probability than 22/23 by HMM |
| IgSP-NBN104 | 0.941 | 0.819 | 0.654 | 19/20 | 1.000 | 0.446* | (22/23) | Cleavage site at 19/20 predicted with lower probability than 22/23 by HMM |
| IgSP-NBN102 | 0.915 | 0.814 | 0.692 | 19/20 | 0.999 | 0.585 | 19/20 | |
| IgSP-NBN99 | 0.906 | 0.833 | 0.798 | 19/20 | 0.998 | 0.722 | 19/20 | |
| Cuttoff values | 0.48 | 0.43 | 0.32 | | 0.5 | | | |

[2]MKCSWVIFFLMAVVTGVNS - 19 amino acids
*Below cuttoff values

SEQUENCES

| SEQ ID NO | TYPE | DESCRIPTION |
|---|---|---|
| 1 | P | IgSP human |
| 2 | P | IgSP Monkey |
| 3 | P | IgSP Marmoset |
| 4 | P | IgSP Mouse |
| 5 | P | IgSP Pig |
| 6 | P | IgSP Rat |
| 7 | N | Nucleotide sequence of chimeric mouse IgSP-human 113 NBN construct |
| 8 | N | Spliced transcript of SEQ ID No 7 |
| 9 | P | Chimeric protein encoded by SEQ ID No 8 and 7) |
| 10 | P | Human pre-pro Neublastin |
| 11 | P | Mouse pre-pro Neublastin |
| 12 | P | Rat pre-pro Neublastin |
| 13 | P | Mature Human 116 amino acid (aa) Neublastin |
| 14 | P | Mature Human 113 aa Neublastin |
| 15 | P | Mature mouse 119 aa Neublastin |
| 16 | P | Mature mouse 116 aa Neublastin |
| 17 | P | Mature rat 116 aa Neublastin |
| 18 | P | Mature rat 113 aa Neublastin |
| 19 | P | N-truncated human 104 aa Neublastin |
| 20 | P | N-truncated human 99 aa Neublastin |
| 21 | P | N-truncated human 140 aa Neublastin |
| 22 | P | N-truncated human 106 aa Neublastin |
| 23 | P | N-truncated human 102 aa Neublastin |
| 24 | P | Human NBN-SP |
| 25 | P | deltaproNBN140 |
| 26 | P | deltaproNBN113 |
| 27 | P | deltaproNBN106 |
| 28 | P | deltaproNBN104 |
| 29 | P | deltaproNBN102 |
| 30 | P | deltaproNBN99 |
| 31 | P | Chimeric mouse IgSP - human 140NBN protein |
| 32 | P | Chimeric mouse IgSP - human 113NBN protein |
| 33 | P | Chimeric mouse IgSP - human 106NBN protein |
| 34 | P | Chimeric mouse IgSP - human 104NBN protein |
| 35 | P | Chimeric mouse IgSP - human 102NBN protein |
| 36 | P | Chimeric mouse IgSP - human 99NBN protein |
| 37 | N | deltaproNBN113 nucleotide sequence |

The invention claimed is:

1. A method for producing a secreted biologically active neublastin (NBN) polypeptide, comprising culturing an eukaryotic cell comprising an expression vector comprising a nucleic acid comprising a promoter sequence operatively linked to a nucleotide sequence encoding an immunoglobulin signal peptide (IgSP) and a neublastin polypeptide, wherein the neublastin polypeptide comprises an amino acid sequence of at least about 95% sequence identity to SEQ ID NO: 13, SEQ ID NO: 14, SEQ ID NO: 19, SEQ ID NO: 20, SEQ ID NO: 22, or SEQ ID NO: 23, wherein said polypeptide induces RET dimerization and autophosphorylation, and wherein said nucleotide sequence does not encode a functional neublastin proregion.

2. The method according to claim 1, wherein the immunoglobulin signal peptide is selected from the group consisting of mouse IgSP (SEQ ID NO: 4), rat IgSP (SEQ ID NO: 6), porcine IgSP (SEQ ID NO: 5), monkey IgSP (SEQ ID NO: 2 or 3), and human IgSP (SEQ ID NO: 1).

3. The method of claim 2, wherein the IgSP is mouse IgSP (SEQ ID NO: 4).

4. The method of claim 2, wherein the IgSP is human IgSP (SEQ ID NO: 1).

5. The method according to claim 1, wherein the neublastin polypeptide comprises the amino acid sequence selected from the group consisting of SEQ ID NO: 13, SEQ ID NO: 14, SEQ ID NO: 19, SEQ ID NO: 20, SEQ ID NO: 22, and SEQ ID NO: 23.

6. The method of claim 5, wherein the neublastin polypeptide is selected from the group consisting of SEQ ID NO: 13 and SEQ ID NO: 14.

7. The method of claim 6, wherein the neublastin polypeptide is human mature 113NBN (SEQ ID NO: 14).

8. The method according to claim 1, wherein the vector is a plasmid.

9. The method according to claim 1, wherein the vector is a virus vector.

10. The method according to claim 9, wherein the vector is selected from the group consisting of HIV, SIV, FIV, EIAV, AAV, adenovirus, retrovirus, herpes virus, and MoMLV.

11. The method according to claim 1, wherein the vector is a mammalian expression vector.

12. The method according to claim 11, wherein the vector is a replication-defective lentivirus particle.

13. The method according to claim 12, wherein said vector particle being produced from a lentiviral vector comprises a 5' lentiviral LTR, a tRNA binding site, a packaging signal, a promoter operably linked to a polynucleotide signal encoding said signal peptide and neublastin polypeptide, an origin of second strand, DNA synthesis and a 3' lentiviral LTR.

14. The method according to claim 1, wherein the promoter capable of directing the expression of the fusion protein is selected from the group consisting of: ubiquitin promoter, CMV promoter, JeT promoter, SV40 promoter, Elongation Factor 1 alpha promoter (EF1-alpha), chick beta-actin, PGK, and MT-1.

15. The method according to claim 1, wherein the promoter is an inducible/repressible promoter.

16. The method according to claim 1, wherein the cell is a mammalian host cell.

17. The method of claim 16, wherein said mammal is selected from the group consisting of rodent, rabbit, dog, cat, pig, monkey, and human cell.

18. The method of claim 16, being selected from the group consisting of CHO, HEK293, COS, PC12, HiB5, RN33b, neuronal cells, fetal cells, ARPE-19, C2C12, HeLa, HepG2, immortalised fibroblast cells, primary and immortalised Retinal Pigment Epithelial (RPE) cells, striatal cells, neurons, astrocytes, and interneurons.

19. The method of claim 1, wherein the neublastin polypeptide is at least about 97% identical to SEQ ID NO: 13, SEQ ID NO: 14, SEQ ID NO: 19, SEQ ID NO: 20, SEQ ID NO: 22, or SEQ ID NO: 23.

20. The method of claim 1, wherein the neublastin polypeptide is at least about 95% identical to SEQ ID NO: 13.

21. The method of claim 1, wherein the neublastin polypeptide is at least about 95% identical to SEQ ID NO: 14.

22. The method of claim 1, wherein the neublastin polypeptide is at least about 95% identical to SEQ ID NO: 19.

23. The method of claim 1, wherein the neublastin polypeptide is at least about 95% identical to SEQ ID NO: 20.

24. The method of claim 1, wherein the neublastin polypeptide is at least about 95% identical to SEQ ID NO: 22.

25. The method of claim 1, wherein the neublastin polypeptide is at least about 95% identical to SEQ ID NO: 23.

26. An expression vector comprising promoter sequence to drive expression in an eukaryotic cell operatively linked to a nucleotide sequence encoding an immunoglobulin signal peptide (IgSP) and a neublastin polypeptide, wherein the neublastin polypeptide comprises an amino acid sequence of at least about 95% sequence identity to SEQ ID NO: 13, SEQ ID NO: 14, SEQ ID NO: 19, SEQ ID NO: 20, SEQ ID NO: 22, or SEQ ID NO: 23, wherein said polypeptide induces RET dimerization and autophosphorylation, and wherein said nucleotide sequence does not encode a functional neublastin proregion.

27. The expression vector according to claim 26, wherein the neublastin polypeptide is at least about 97% identical to SEQ ID NO: 13, SEQ ID NO: 14, SEQ ID NO: 19, SEQ ID NO: 20, SEQ ID NO: 22, or SEQ ID NO: 23.

28. The expression vector according to claim 26, wherein the neublastin polypeptide is at least about 95% identical to SEQ ID NO: 13.

29. The expression vector according to claim 26, wherein the neublastin polypeptide is at least about 95% identical to SEQ ID NO: 14.

30. The expression vector according to claim 26, wherein the neublastin polypeptide is at least about 95% identical to SEQ ID NO: 19.

31. The expression vector according to claim 26, wherein the neublastin polypeptide is at least about 95% identical to SEQ ID NO: 20.

32. The expression vector according to claim 26, wherein the neublastin polypeptide is at least about 95% identical to SEQ ID NO: 22.

33. The expression vector according to claim 26, wherein the neublastin polypeptide is at least about 95% identical to SEQ ID NO: 23.

34. An isolated eukaryotic host cell transduced or transfected with an expression vector, wherein the expression vector comprises a polynucleotide sequence encoding an immunoglobulin signal peptide (IgSP) operatively linked to a neublastin polypeptide, wherein the neublastin polypeptide comprises an amino acid sequence of at least about 95% sequence identity to SEQ ID NO: 13, SEQ ID NO: 14, SEQ ID NO: 19, SEQ ID NO: 20, SEQ ID NO: 22, or SEQ ID NO: 23, wherein said polypeptide induces RET dimerization and autophosphorylation, and wherein said nucleotide sequence does not encode a functional neublastin proregion.

35. The cell according to claim 34, wherein the cell is a mammalian cell.

36. The cell according to claim 35, wherein the cell is capable of secreting neublastin or a functional equivalent thereof in amounts in excess of 500 ng/106 cells/24 hours.

37. The mammalian cell according to claim 35, being selected from the group consisting of CHO, HEK293 COS, PC12, HiB5, RN33b, C2C12, HeLa, HepG2, primary and immortalised Retinal Pigment Epithelial (RPE) cells, and ARPE-19 cells.

38. The mammalian cell according to claim 35, being selected from the group consisting of CHO, HEK293, COS, and ARPE-19.

39. The mammalian cell according to claim 35, being selected from the group consisting of RPE cells, neuronal cells, neuronal precursor cells, stem cells, and fetal cells.

40. The mammalian cell according to claim 35, being attached to a support matrix.

41. The cell according to claim 34, wherein the neublastin polypeptide is at least about 97% identical to SEQ ID NO: 13, SEQ ID NO: 14, SEQ ID NO: 19, SEQ ID NO: 20, SEQ ID NO: 22, or SEQ ID NO: 23.

42. The cell according to claim 34, wherein the neublastin polypeptide is at least about 95% identical to SEQ ID NO: 13.

43. The cell according to claim 34, wherein the neublastin polypeptide is at least about 95% identical to SEQ ID NO: 14.

44. The cell according to claim 34, wherein the neublastin polypeptide is at least about 95% identical to SEQ ID NO: 19.

45. The cell according to claim 34, wherein the neublastin polypeptide is at least about 95% identical to SEQ ID NO: 20.

46. The cell according to claim 34, wherein the neublastin polypeptide is at least about 95% identical to SEQ ID NO: 22.

47. The cell according to claim 34, wherein the neublastin polypeptide is at least about 95% identical to SEQ ID NO: 23.

\* \* \* \* \*

UNITED STATES PATENT AND TRADEMARK OFFICE
CERTIFICATE OF CORRECTION

| | | |
|---|---|---|
| PATENT NO. | : 7,601,518 B2 | Page 1 of 1 |
| APPLICATION NO. | : 11/864891 | |
| DATED | : October 13, 2009 | |
| INVENTOR(S) | : Wahlberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 433 days.

Signed and Sealed this
Twenty-second Day of February, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,518 B2 | Page 1 of 1 |
| APPLICATION NO. | : 10/864891 | |
| DATED | : October 13, 2009 | |
| INVENTOR(S) | : Wahlberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 433 days.

This certificate supersedes the Certificate of Correction issued February 22, 2011.

Signed and Sealed this
Seventeenth Day of May, 2011

David J. Kappos
*Director of the United States Patent and Trademark Office*

SEQUENCE LISTING

<160> NUMBER OF SEQ ID NOS: 37

<210> SEQ ID NO 1
<211> LENGTH: 19
<212> TYPE: PRT
<213> ORGANISM: Homo sapiens

<400> SEQUENCE: 1

Met Asp Cys Thr Trp Arg Ile Leu Phe Leu Val Ala Ala Ala Thr Gly
1               5                   10                  15

Thr His Ala

<210> SEQ ID NO 2
<211> LENGTH: 19
<212> TYPE: PRT
<213> ORGANISM: Macaca mulatta

<400> SEQUENCE: 2

Met Lys His Leu Trp Phe Phe Leu Leu Leu Val Ala Ala Pro Arg Trp
1               5                   10                  15

Val Leu Ser

<210> SEQ ID NO 3
<211> LENGTH: 19
<212> TYPE: PRT
<213> ORGANISM: Callithrix jacchus

<400> SEQUENCE: 3

Met Asp Trp Thr Trp Arg Ile Phe Leu Leu Val Ala Thr Ala Thr Gly
1               5                   10                  15

Ala His Ser

<210> SEQ ID NO 4
<211> LENGTH: 19
<212> TYPE: PRT
<213> ORGANISM: Mus musculus

<400> SEQUENCE: 4

Met Lys Cys Ser Trp Val Ile Phe Phe Leu Met Ala Val Val Thr Gly
1               5                   10                  15

Val Asn Ser

<210> SEQ ID NO 5
<211> LENGTH: 19
<212> TYPE: PRT
<213> ORGANISM: Sus scrofa

<400> SEQUENCE: 5

Met Glu Phe Arg Leu Asn Trp Val Val Leu Phe Ala Leu Leu Gln Gly
1               5                   10                  15

Val Gln Gly

<210> SEQ ID NO 6
<211> LENGTH: 19
<212> TYPE: PRT
<213> ORGANISM: Rattus norvegicus

<400> SEQUENCE: 6

Met Lys Cys Ser Trp Ile Ile Leu Phe Leu Met Ala Leu Thr Thr Gly
1               5                   10                  15

Val Asn Ser

```
<210> SEQ ID NO 7
<211> LENGTH: 478
<212> TYPE: DNA
<213> ORGANISM: artificial sequence
<220> FEATURE:
<223> OTHER INFORMATION: murine IgSP - human NBN113
<220> FEATURE:
<221> NAME/KEY: Intron
<222> LOCATION: (47)..(125)
<223> OTHER INFORMATION:
<220> FEATURE:
<221> NAME/KEY: exon
<222> LOCATION: (1)..(46)
<223> OTHER INFORMATION:
<220> FEATURE:
<221> NAME/KEY: exon
<222> LOCATION: (126)..(478)
<223> OTHER INFORMATION:

<400> SEQUENCE: 7
```

| | | |
|---|---|---|
| atg aaa tgc agc tgg gtt atc ttc ttc ctg atg gca gtg gtt aca g | 46 | |
| Met Lys Cys Ser Trp Val Ile Phe Phe Leu Met Ala Val Val Thr | | |
| 1               5                   10                  15 | | |
| gtaaggggct cccaagtccc aaacttgagg gtccataaac tctgtgacag tggcaatcac | 106 | |
| tttgcctttc tttctacag gg gtg aat tcg gct ggg ggc ccg ggc agc cgc | 157 | |
|                               Gly Val Asn Ser Ala Gly Gly Pro Gly Ser Arg | | |
|                                    20                  25 | | |
| gct cgg gca gcg ggg gcg cgg ggc tgc cgc ctg cgc tcg cag ctg gtg | 205 | |
| Ala Arg Ala Ala Gly Ala Arg Gly Cys Arg Leu Arg Ser Gln Leu Val | | |
|     30                  35                  40 | | |
| ccg gtg cgc gcg ctc ggc ctg ggc cac cgc tcc gac gag ctg gtg cgt | 253 | |
| Pro Val Arg Ala Leu Gly Leu Gly His Arg Ser Asp Glu Leu Val Arg | | |
|         45                  50                  55 | | |
| ttc cgc ttc tgc agc ggc tcc tgc cgc cgc gcg cgc tct cca cac gac | 301 | |
| Phe Arg Phe Cys Ser Gly Ser Cys Arg Arg Ala Arg Ser Pro His Asp | | |
|           60                  65                  70 | | |
| ctc agc ctg gcc agc cta ctg ggc gcc ggg gcc ctg cga ccg ccc ccg | 349 | |
| Leu Ser Leu Ala Ser Leu Leu Gly Ala Gly Ala Leu Arg Pro Pro Pro | | |
| 75                  80                  85                  90 | | |
| ggc tcc cgg ccc gtc agc cag ccc tgc tgc cga ccc acg cgc tac gaa | 397 | |
| Gly Ser Arg Pro Val Ser Gln Pro Cys Cys Arg Pro Thr Arg Tyr Glu | | |
|               95                  100                 105 | | |
| gcg gtc tcc ttc atg gac gtc aac agc acc tgg aga acc gtg gac cgc | 445 | |
| Ala Val Ser Phe Met Asp Val Asn Ser Thr Trp Arg Thr Val Asp Arg | | |
|             110                 115                 120 | | |
| ctc tcc gcc acc gcc tgc ggc tgc ctg ggc tga | 478 | |
| Leu Ser Ala Thr Ala Cys Gly Cys Leu Gly | | |
|         125                 130 | | |

```
<210> SEQ ID NO 8
<211> LENGTH: 399
<212> TYPE: DNA
<213> ORGANISM: artificial sequence
<220> FEATURE:
<223> OTHER INFORMATION: Murine IgSP - human NBN113
<220> FEATURE:
<221> NAME/KEY: CDS
<222> LOCATION: (1)..(399)
<223> OTHER INFORMATION:
<220> FEATURE:
<221> NAME/KEY: sig_peptide
<222> LOCATION: (1)..(57)
<223> OTHER INFORMATION: Murine IgSP
<220> FEATURE:
```

<221> NAME/KEY: misc_feature
<222> LOCATION: (58)..(396)
<223> OTHER INFORMATION: Human 113 Neublastin

<400> SEQUENCE: 8

```
atg aaa tgc agc tgg gtt atc ttc ttc ctg atg gca gtg gtt aca ggg        48
Met Lys Cys Ser Trp Val Ile Phe Phe Leu Met Ala Val Val Thr Gly
1               5                   10                  15 gtg aat tcg gct ggg ggc ccg ggc agc cgc gct cgg gca gcg ggg gcg        96
Val Asn Ser Ala Gly Gly Pro Gly Ser Arg Ala Arg Ala Ala Gly Ala
                20                  25                  30 cgg ggc tgc cgc ctg cgc tcg cag ctg gtg ccg gtg cgc gcg ctc ggc       144
Arg Gly Cys Arg Leu Arg Ser Gln Leu Val Pro Val Arg Ala Leu Gly
            35                  40                  45 ctg ggc cac cgc tcc gac gag ctg gtg cgt ttc cgc ttc tgc agc ggc       192
Leu Gly His Arg Ser Asp Glu Leu Val Arg Phe Arg Phe Cys Ser Gly
        50                  55                  60 tcc tgc cgc cgc gcg cgc tct cca cac gac ctc agc ctg gcc agc cta       240
Ser Cys Arg Arg Ala Arg Ser Pro His Asp Leu Ser Leu Ala Ser Leu
65                  70                  75                  80 ctg ggc gcc ggg gcc ctg cga ccg ccc ccg ggc tcc cgg ccc gtc agc       288
Leu Gly Ala Gly Ala Leu Arg Pro Pro Pro Gly Ser Arg Pro Val Ser
                85                  90                  95 cag ccc tgc tgc cga ccc acg cgc tac gaa gcg gtc tcc ttc atg gac       336
Gln Pro Cys Cys Arg Pro Thr Arg Tyr Glu Ala Val Ser Phe Met Asp
                100                 105                 110 gtc aac agc acc tgg aga acc gtg gac cgc ctc tcc gcc acc gcc tgc       384
Val Asn Ser Thr Trp Arg Thr Val Asp Arg Leu Ser Ala Thr Ala Cys
            115                 120                 125 ggc tgc ctg ggc tga                                                    399
Gly Cys Leu Gly
        130
```

<210> SEQ ID NO 9
<211> LENGTH: 132
<212> TYPE: PRT
<213> ORGANISM: artificial sequence
<220> FEATURE:
<223> OTHER INFORMATION: Murine IgSP - human NBN113
<220> FEATURE:
<221> NAME/KEY: misc_feature
<222> LOCATION: (58)..(396)
<223> OTHER INFORMATION: Human 113 Neublastin

<400> SEQUENCE: 9

```
Met Lys Cys Ser Trp Val Ile Phe Phe Leu Met Ala Val Val Thr Gly
1               5                   10                  15

Val Asn Ser Ala Gly Gly Pro Gly Ser Arg Ala Arg Ala Ala Gly Ala
                20                  25                  30

Arg Gly Cys Arg Leu Arg Ser Gln Leu Val Pro Val Arg Ala Leu Gly
            35                  40                  45

Leu Gly His Arg Ser Asp Glu Leu Val Arg Phe Arg Phe Cys Ser Gly
        50                  55                  60

Ser Cys Arg Arg Ala Arg Ser Pro His Asp Leu Ser Leu Ala Ser Leu
65                  70                  75                  80

Leu Gly Ala Gly Ala Leu Arg Pro Pro Pro Gly Ser Arg Pro Val Ser
                85                  90                  95

Gln Pro Cys Cys Arg Pro Thr Arg Tyr Glu Ala Val Ser Phe Met Asp
                100                 105                 110

Val Asn Ser Thr Trp Arg Thr Val Asp Arg Leu Ser Ala Thr Ala Cys
            115                 120                 125
```

-continued

Gly Cys Leu Gly
    130

<210> SEQ ID NO 10
<211> LENGTH: 220
<212> TYPE: PRT
<213> ORGANISM: Homo sapiens
<220> FEATURE:
<221> NAME/KEY: misc_feature
<223> OTHER INFORMATION: Full length human Neublastin
<220> FEATURE:
<221> NAME/KEY: signal
<222> LOCATION: (1)..(39)
<223> OTHER INFORMATION:
<220> FEATURE:
<221> NAME/KEY: PROPEP
<222> LOCATION: (40)..(80)
<223> OTHER INFORMATION:
<220> FEATURE:
<221> NAME/KEY: mat_peptide
<222> LOCATION: (81)..()
<223> OTHER INFORMATION:

<400> SEQUENCE: 10

Met Glu Leu Gly Leu Gly Gly Leu Ser Thr Leu Ser His Cys Pro Trp
-80                 -75                 -70                 -65

Pro Arg Arg Gln Pro Ala Leu Trp Pro Thr Leu Ala Ala Leu Ala Leu
            -60                 -55                 -50

Leu Ser Ser Val Ala Glu Ala Ser Leu Gly Ser Ala Pro Arg Ser Pro
            -45                 -40                 -35

Ala Pro Arg Glu Gly Pro Pro Pro Val Leu Ala Ser Pro Ala Gly His
            -30                 -25                 -20

Leu Pro Gly Gly Arg Thr Ala Arg Trp Cys Ser Gly Arg Ala Arg Arg
    -15                 -10                  -5                  -1

Pro Pro Pro Gln Pro Ser Arg Pro Ala Pro Pro Pro Ala Pro Pro
1                    5                  10                  15

Ser Ala Leu Pro Arg Gly Gly Arg Ala Ala Arg Ala Gly Gly Pro Gly
            20                  25                  30

Ser Arg Ala Arg Ala Ala Gly Ala Arg Gly Cys Arg Leu Arg Ser Gln
            35                  40                  45

Leu Val Pro Val Arg Ala Leu Gly Leu Gly His Arg Ser Asp Glu Leu
    50                  55                  60

Val Arg Phe Arg Phe Cys Ser Gly Ser Cys Arg Arg Ala Arg Ser Pro
65                  70                  75                  80

His Asp Leu Ser Leu Ala Ser Leu Leu Gly Ala Gly Ala Leu Arg Pro
            85                  90                  95

Pro Pro Gly Ser Arg Pro Val Ser Gln Pro Cys Cys Arg Pro Thr Arg
            100                 105                 110

Tyr Glu Ala Val Ser Phe Met Asp Val Asn Ser Thr Trp Arg Thr Val
            115                 120                 125

Asp Arg Leu Ser Ala Thr Ala Cys Gly Cys Leu Gly
    130                 135                 140

<210> SEQ ID NO 11
<211> LENGTH: 224
<212> TYPE: PRT
<213> ORGANISM: Mus musculus
<220> FEATURE:
<221> NAME/KEY: SIGNAL
<222> LOCATION: (1)..(39)
<223> OTHER INFORMATION:
<220> FEATURE:

```
<221> NAME/KEY: PROPEP
<222> LOCATION: (40)..(80)
<223> OTHER INFORMATION:
<220> FEATURE:
<221> NAME/KEY: mat_peptide
<222> LOCATION: (81)..()
<223> OTHER INFORMATION:

<400> SEQUENCE: 11
```

Met Glu Leu Gly Leu Ala Glu Pro Thr Ala Leu Ser His Cys Leu Arg
-80                 -75                 -70                 -65

Pro Arg Trp Gln Ser Ala Trp Pro Thr Leu Ala Val Leu Ala Leu
            -60                 -55                 -50

Leu Ser Cys Val Thr Glu Ala Ser Leu Asp Pro Met Ser Arg Ser Pro
                -45                 -40                 -35

Ala Ala Arg Asp Gly Pro Ser Pro Val Leu Ala Pro Thr Asp His
        -30                 -25                 -20

Leu Pro Gly Gly His Thr Ala His Leu Cys Ser Glu Arg Thr Leu Arg
        -15                 -10                  -5                  -1

Pro Pro Pro Gln Ser Pro Gln Pro Ala Pro Pro Pro Gly Pro Ala
 1               5                  10                  15

Leu Gln Ser Pro Pro Ala Ala Leu Arg Gly Ala Arg Ala Arg Ala
                20                  25                  30

Gly Thr Arg Ser Ser Arg Ala Arg Thr Thr Asp Ala Arg Gly Cys Arg
            35                  40                  45

Leu Arg Ser Gln Leu Val Pro Val Ser Ala Leu Gly Leu Gly His Ser
 50                  55                  60

Ser Asp Glu Leu Ile Arg Phe Arg Phe Cys Ser Gly Ser Cys Arg Arg
 65                  70                  75                  80

Ala Arg Ser Gln His Asp Leu Ser Leu Ala Ser Leu Leu Gly Ala Gly
                85                  90                  95

Ala Leu Arg Ser Pro Pro Gly Ser Arg Pro Ile Ser Gln Pro Cys Cys
                100                 105                 110

Arg Pro Thr Arg Tyr Glu Ala Val Ser Phe Met Asp Val Asn Ser Thr
            115                 120                 125

Trp Arg Thr Val Asp His Leu Ser Ala Thr Ala Cys Gly Cys Leu Gly
            130                 135                 140

```
<210> SEQ ID NO 12
<211> LENGTH: 224
<212> TYPE: PRT
<213> ORGANISM: Rattus norvegicus
<220> FEATURE:
<221> NAME/KEY: SIGNAL
<222> LOCATION: (1)..(39)
<223> OTHER INFORMATION:
<220> FEATURE:
<221> NAME/KEY: PROPEP
<222> LOCATION: (40)..(80)
<223> OTHER INFORMATION:
<220> FEATURE:
<221> NAME/KEY: mat_peptide
<222> LOCATION: (81)..()
<223> OTHER INFORMATION:

<400> SEQUENCE: 12
```

Met Glu Leu Gly Leu Gly Glu Pro Thr Ala Leu Ser His Cys Leu Arg
-80                 -75                 -70                 -65

Pro Arg Trp Gln Pro Ala Leu Trp Pro Thr Leu Ala Ala Leu Ala Leu
            -60                 -55                 -50

Leu Ser Ser Val Thr Glu Ala Ser Leu Asp Pro Met Ser Arg Ser Pro

```
                    -45              -40              -35
Ala Ser Arg Asp Val Pro Ser Pro Val Leu Ala Pro Pro Thr Asp Tyr
    -30              -25              -20

Leu Pro Gly Gly His Thr Ala His Leu Cys Ser Glu Arg Ala Leu Arg
    -15              -10              -5               -1

Pro Pro Pro Gln Ser Pro Gln Pro Ala Pro Pro Pro Gly Pro Pro Ala
1               5                   10              15

Leu Gln Ser Pro Pro Ala Ala Leu Arg Gly Ala Arg Ala Ala Arg Ala
                20              25              30

Gly Thr Arg Ser Ser Arg Ala Arg Ala Thr Asp Ala Arg Gly Cys Arg
        35              40              45

Leu Arg Ser Gln Leu Val Pro Val Ser Ala Leu Gly Leu Gly His Ser
    50              55              60

Ser Asp Glu Leu Ile Arg Phe Arg Phe Cys Ser Gly Ser Cys Arg Arg
65              70              75              80

Ala Arg Ser Pro His Asp Leu Ser Leu Ala Ser Leu Leu Asp Ala Gly
                85              90              95

Ala Leu Arg Ser Pro Pro Gly Ser Arg Pro Ile Ser Gln Pro Cys Cys
                100             105             110

Arg Pro Thr Arg Tyr Glu Ala Val Ser Phe Met Asp Val Asn Ser Thr
            115             120             125

Trp Arg Thr Val Asp His Leu Ser Ala Thr Ala Cys Gly Cys Leu Gly
            130             135             140
```

```
<210> SEQ ID NO 13
<211> LENGTH: 116
<212> TYPE: PRT
<213> ORGANISM: Homo sapiens

<400> SEQUENCE: 13

Ala Ala Arg Ala Gly Gly Pro Gly Ser Arg Ala Arg Ala Ala Gly Ala
1               5                   10              15

Arg Gly Cys Arg Leu Arg Ser Gln Leu Val Pro Val Arg Ala Leu Gly
                20              25              30

Leu Gly His Arg Ser Asp Glu Leu Val Arg Phe Arg Phe Cys Ser Gly
        35              40              45

Ser Cys Arg Arg Ala Arg Ser Pro His Asp Leu Ser Leu Ala Ser Leu
    50              55              60

Leu Gly Ala Gly Ala Leu Arg Pro Pro Gly Ser Arg Pro Val Ser
65              70              75              80

Gln Pro Cys Cys Arg Pro Thr Arg Tyr Glu Ala Val Ser Phe Met Asp
                85              90              95

Val Asn Ser Thr Trp Arg Thr Val Asp Arg Leu Ser Ala Thr Ala Cys
                100             105             110

Gly Cys Leu Gly
        115
```

```
<210> SEQ ID NO 14
<211> LENGTH: 113
<212> TYPE: PRT
<213> ORGANISM: Homo sapiens

<400> SEQUENCE: 14

Ala Gly Gly Pro Gly Ser Arg Ala Arg Ala Ala Gly Ala Arg Gly Cys
1               5                   10              15

Arg Leu Arg Ser Gln Leu Val Pro Val Arg Ala Leu Gly Leu Gly His
```

```
            20                  25                  30
Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 15
<211> LENGTH: 119
<212> TYPE: PRT
<213> ORGANISM: Mus musculus

<400> SEQUENCE: 15

Gly Ala Arg Ala Ala Arg Ala Gly Thr Arg Ser Ser Arg Ala Arg Thr
1               5                   10                  15

Thr Asp Ala Arg Gly Cys Arg Leu Arg Ser Gln Leu Val Pro Val Ser
            20                  25                  30

Ala Leu Gly Leu Gly His Ser Ser Asp Glu Leu Ile Arg Phe Arg Phe
        35                  40                  45

Cys Ser Gly Ser Cys Arg Arg Ala Arg Ser Gln His Asp Leu Ser Leu
    50                  55                  60

Ala Ser Leu Leu Gly Ala Gly Ala Leu Arg Ser Pro Pro Gly Ser Arg
65                  70                  75                  80

Pro Ile Ser Gln Pro Cys Cys Arg Pro Thr Arg Tyr Glu Ala Val Ser
                85                  90                  95

Phe Met Asp Val Asn Ser Thr Trp Arg Thr Val Asp His Leu Ser Ala
            100                 105                 110

Thr Ala Cys Gly Cys Leu Gly
        115

<210> SEQ ID NO 16
<211> LENGTH: 116
<212> TYPE: PRT
<213> ORGANISM: Mus musculus

<400> SEQUENCE: 16

Ala Ala Arg Ala Gly Thr Arg Ser Ser Arg Ala Arg Thr Thr Asp Ala
1               5                   10                  15

Arg Gly Cys Arg Leu Arg Ser Gln Leu Val Pro Val Ser Ala Leu Gly
            20                  25                  30

Leu Gly His Ser Ser Asp Glu Leu Ile Arg Phe Arg Phe Cys Ser Gly
        35                  40                  45

Ser Cys Arg Arg Ala Arg Ser Gln His Asp Leu Ser Leu Ala Ser Leu
    50                  55                  60

Leu Gly Ala Gly Ala Leu Arg Ser Pro Pro Gly Ser Arg Pro Ile Ser
65                  70                  75                  80

Gln Pro Cys Cys Arg Pro Thr Arg Tyr Glu Ala Val Ser Phe Met Asp
                85                  90                  95

Val Asn Ser Thr Trp Arg Thr Val Asp His Leu Ser Ala Thr Ala Cys
            100                 105                 110
```

Gly Cys Leu Gly
        115

<210> SEQ ID NO 17
<211> LENGTH: 116
<212> TYPE: PRT
<213> ORGANISM: Rattus norvegicus

<400> SEQUENCE: 17

Ala Ala Arg Ala Gly Thr Arg Ser Ser Arg Ala Arg Ala Thr Asp Ala
1               5                   10                  15

Arg Gly Cys Arg Leu Arg Ser Gln Leu Val Pro Val Ser Ala Leu Gly
            20                  25                  30

Leu Gly His Ser Ser Asp Glu Leu Ile Arg Phe Arg Phe Cys Ser Gly
        35                  40                  45

Ser Cys Arg Arg Ala Arg Ser Pro His Asp Leu Ser Leu Ala Ser Leu
    50                  55                  60

Leu Asp Ala Gly Ala Leu Arg Ser Pro Pro Gly Ser Arg Pro Ile Ser
65                  70                  75                  80

Gln Pro Cys Cys Arg Pro Thr Arg Tyr Glu Ala Val Ser Phe Met Asp
                85                  90                  95

Val Asn Ser Thr Trp Arg Thr Val Asp His Leu Ser Ala Thr Ala Cys
            100                 105                 110

Gly Cys Leu Gly
        115

<210> SEQ ID NO 18
<211> LENGTH: 113
<212> TYPE: PRT
<213> ORGANISM: Rattus norvegicus

<400> SEQUENCE: 18

Ala Gly Thr Arg Ser Ser Arg Ala Arg Ala Thr Asp Ala Arg Gly Cys
1               5                   10                  15

Arg Leu Arg Ser Gln Leu Val Pro Val Ser Ala Leu Gly Leu Gly His
            20                  25                  30

Ser Ser Asp Glu Leu Ile Arg Phe Arg Phe Cys Ser Gly Ser Cys Arg
        35                  40                  45

Arg Ala Arg Ser Pro His Asp Leu Ser Leu Ala Ser Leu Leu Asp Ala
    50                  55                  60

Gly Ala Leu Arg Ser Pro Pro Gly Ser Arg Pro Ile Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp His Leu Ser Ala Thr Ala Cys Gly Cys Leu
            100                 105                 110

Gly

<210> SEQ ID NO 19
<211> LENGTH: 104
<212> TYPE: PRT
<213> ORGANISM: Homo sapiens

<400> SEQUENCE: 19

Ala Ala Gly Ala Arg Gly Cys Arg Leu Arg Ser Gln Leu Val Pro Val
1               5                   10                  15

Arg Ala Leu Gly Leu Gly His Arg Ser Asp Glu Leu Val Arg Phe Arg

```
                20                  25                  30
Phe Cys Ser Gly Ser Cys Arg Arg Ala Arg Ser Pro His Asp Leu Ser
        35                  40                  45

Leu Ala Ser Leu Leu Gly Ala Gly Ala Leu Arg Pro Pro Gly Ser
    50                  55                  60

Arg Pro Val Ser Gln Pro Cys Cys Arg Pro Thr Arg Tyr Glu Ala Val
65                  70                  75                  80

Ser Phe Met Asp Val Asn Ser Thr Trp Arg Thr Val Asp Arg Leu Ser
                85                  90                  95

Ala Thr Ala Cys Gly Cys Leu Gly
            100

<210> SEQ ID NO 20
<211> LENGTH: 99
<212> TYPE: PRT
<213> ORGANISM: Homo sapiens

<400> SEQUENCE: 20

Gly Cys Arg Leu Arg Ser Gln Leu Val Pro Val Arg Ala Leu Gly Leu
1               5                   10                  15

Gly His Arg Ser Asp Glu Leu Val Arg Phe Arg Phe Cys Ser Gly Ser
                20                  25                  30

Cys Arg Arg Ala Arg Ser Pro His Asp Leu Ser Leu Ala Ser Leu Leu
            35                  40                  45

Gly Ala Gly Ala Leu Arg Pro Pro Gly Ser Arg Pro Val Ser Gln
        50                  55                  60

Pro Cys Cys Arg Pro Thr Arg Tyr Glu Ala Val Ser Phe Met Asp Val
65                  70                  75                  80

Asn Ser Thr Trp Arg Thr Val Asp Arg Leu Ser Ala Thr Ala Cys Gly
                85                  90                  95

Cys Leu Gly

<210> SEQ ID NO 21
<211> LENGTH: 140
<212> TYPE: PRT
<213> ORGANISM: Homo sapiens

<400> SEQUENCE: 21

Pro Pro Pro Gln Pro Ser Arg Pro Ala Pro Pro Pro Ala Pro Pro
1               5                   10                  15

Ser Ala Leu Pro Arg Gly Gly Arg Ala Ala Arg Ala Gly Gly Pro Gly
            20                  25                  30

Ser Arg Ala Arg Ala Ala Gly Ala Arg Gly Cys Arg Leu Arg Ser Gln
            35                  40                  45

Leu Val Pro Val Arg Ala Leu Gly Leu Gly His Arg Ser Asp Glu Leu
    50                  55                  60

Val Arg Phe Arg Phe Cys Ser Gly Ser Cys Arg Arg Ala Arg Ser Pro
65                  70                  75                  80

His Asp Leu Ser Leu Ala Ser Leu Leu Gly Ala Gly Ala Leu Arg Pro
                85                  90                  95

Pro Pro Gly Ser Arg Pro Val Ser Gln Pro Cys Cys Arg Pro Thr Arg
            100                 105                 110

Tyr Glu Ala Val Ser Phe Met Asp Val Asn Ser Thr Trp Arg Thr Val
        115                 120                 125

Asp Arg Leu Ser Ala Thr Ala Cys Gly Cys Leu Gly
    130                 135                 140
```

<210> SEQ ID NO 22
<211> LENGTH: 106
<212> TYPE: PRT
<213> ORGANISM: Homo sapiens

<400> SEQUENCE: 22

Ala Arg Ala Ala Gly Ala Arg Gly Cys Arg Leu Arg Ser Gln Leu Val
1               5                   10                  15

Pro Val Arg Ala Leu Gly Leu Gly His Arg Ser Asp Glu Leu Val Arg
            20                  25                  30

Phe Arg Phe Cys Ser Gly Ser Cys Arg Arg Ala Arg Ser Pro His Asp
        35                  40                  45

Leu Ser Leu Ala Ser Leu Leu Gly Ala Gly Ala Leu Arg Pro Pro Pro
    50                  55                  60

Gly Ser Arg Pro Val Ser Gln Pro Cys Cys Arg Pro Thr Arg Tyr Glu
65                  70                  75                  80

Ala Val Ser Phe Met Asp Val Asn Ser Thr Trp Arg Thr Val Asp Arg
                85                  90                  95

Leu Ser Ala Thr Ala Cys Gly Cys Leu Gly
            100                 105

<210> SEQ ID NO 23
<211> LENGTH: 102
<212> TYPE: PRT
<213> ORGANISM: Homo sapiens

<400> SEQUENCE: 23

Gly Ala Arg Gly Cys Arg Leu Arg Ser Gln Leu Val Pro Val Arg Ala
1               5                   10                  15

Leu Gly Leu Gly His Arg Ser Asp Glu Leu Val Arg Phe Arg Phe Cys
            20                  25                  30

Ser Gly Ser Cys Arg Arg Ala Arg Ser Pro His Asp Leu Ser Leu Ala
        35                  40                  45

Ser Leu Leu Gly Ala Gly Ala Leu Arg Pro Pro Gly Ser Arg Pro
    50                  55                  60

Val Ser Gln Pro Cys Cys Arg Pro Thr Arg Tyr Glu Ala Val Ser Phe
65                  70                  75                  80

Met Asp Val Asn Ser Thr Trp Arg Thr Val Asp Arg Leu Ser Ala Thr
                85                  90                  95

Ala Cys Gly Cys Leu Gly
            100

<210> SEQ ID NO 24
<211> LENGTH: 39
<212> TYPE: PRT
<213> ORGANISM: Homo sapiens

<400> SEQUENCE: 24

Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
            20                  25                  30

Leu Ser Ser Val Ala Glu Ala
            35

<210> SEQ ID NO 25
<211> LENGTH: 179

```
<212> TYPE: PRT
<213> ORGANISM: artificial sequence
<220> FEATURE:
<223> OTHER INFORMATION: deltapro human NBN140
<220> FEATURE:
<221> NAME/KEY: signal
<222> LOCATION: (1)..(39)
<223> OTHER INFORMATION:
<220> FEATURE:
<221> NAME/KEY: mat_peptide
<222> LOCATION: (40)..()
<223> OTHER INFORMATION:

<400> SEQUENCE: 25

Met Glu Leu Gly Leu Gly Gly Leu Ser Thr Leu Ser His Cys Pro Trp
            -35                 -30                 -25

Pro Arg Arg Gln Pro Ala Leu Trp Pro Thr Leu Ala Ala Leu Ala Leu
            -20                 -15                 -10

Leu Ser Ser Val Ala Glu Ala Pro Pro Gln Pro Ser Arg Pro Ala
         -5             -1  1               5

Pro Pro Pro Pro Ala Pro Ser Ala Leu Pro Arg Gly Gly Arg Ala
 10              15              20              25

Ala Arg Ala Gly Gly Pro Gly Ser Arg Ala Arg Ala Gly Ala Arg
             30              35              40

Gly Cys Arg Leu Arg Ser Gln Leu Val Pro Val Arg Ala Leu Gly Leu
             45                  50                  55

Gly His Arg Ser Asp Glu Leu Val Arg Phe Arg Phe Cys Ser Gly Ser
             60                  65                  70

Cys Arg Arg Ala Arg Ser Pro His Asp Leu Ser Leu Ala Ser Leu Leu
 75                  80                  85

Gly Ala Gly Ala Leu Arg Pro Pro Gly Ser Arg Pro Val Ser Gln
 90              95                  100                 105

Pro Cys Cys Arg Pro Thr Arg Tyr Glu Ala Val Ser Phe Met Asp Val
                 110                 115                 120

Asn Ser Thr Trp Arg Thr Val Asp Arg Leu Ser Ala Thr Ala Cys Gly
                 125                 130                 135

Cys Leu Gly
        140

<210> SEQ ID NO 26
<211> LENGTH: 152
<212> TYPE: PRT
<213> ORGANISM: artificial sequence
<220> FEATURE:
<223> OTHER INFORMATION: deltapro human NBN113
<220> FEATURE:
<221> NAME/KEY: SIGNAL
<222> LOCATION: (1)..(39)
<223> OTHER INFORMATION:
<220> FEATURE:
<221> NAME/KEY: mat_peptide
<222> LOCATION: (40)..()
<223> OTHER INFORMATION:

<400> SEQUENCE: 26

Met Glu Leu Gly Leu Gly Gly Leu Ser Thr Leu Ser His Cys Pro Trp
            -35                 -30                 -25

Pro Arg Arg Gln Pro Ala Leu Trp Pro Thr Leu Ala Ala Leu Ala Leu
            -20                 -15                 -10

Leu Ser Ser Val Ala Glu Ala Ala Gly Gly Pro Gly Ser Arg Ala Arg
         -5             -1  1               5

Ala Ala Gly Ala Arg Gly Cys Arg Leu Arg Ser Gln Leu Val Pro Val
```

```
            10                  15                  20                  25
Arg Ala Leu Gly Leu Gly His Arg Ser Asp Glu Leu Val Arg Phe Arg
                30                  35                  40

Phe Cys Ser Gly Ser Cys Arg Arg Ala Arg Ser Pro His Asp Leu Ser
                45                  50                  55

Leu Ala Ser Leu Leu Gly Ala Gly Ala Leu Arg Pro Pro Gly Ser
            60                  65                  70

Arg Pro Val Ser Gln Pro Cys Cys Arg Pro Thr Arg Tyr Glu Ala Val
            75                  80                  85

Ser Phe Met Asp Val Asn Ser Thr Trp Arg Thr Val Asp Arg Leu Ser
90                  95                  100                 105

Ala Thr Ala Cys Gly Cys Leu Gly
                110

<210> SEQ ID NO 27
<211> LENGTH: 145
<212> TYPE: PRT
<213> ORGANISM: artificial sequence
<220> FEATURE:
<223> OTHER INFORMATION: deltapro human NBN106
<220> FEATURE:
<221> NAME/KEY: signal
<222> LOCATION: (1)..(39)
<223> OTHER INFORMATION:
<220> FEATURE:
<221> NAME/KEY: mat_peptide
<222> LOCATION: (40)..()
<223> OTHER INFORMATION:

<400> SEQUENCE: 27

Met Glu Leu Gly Leu Gly Gly Leu Ser Thr Leu Ser His Cys Pro Trp
                -35                 -30                 -25

Pro Arg Arg Gln Pro Ala Leu Trp Pro Thr Leu Ala Ala Leu Ala Leu
                -20                 -15                 -10

Leu Ser Ser Val Ala Glu Ala Ala Arg Ala Ala Gly Ala Arg Gly Cys
            -5                  -1  1                   5

Arg Leu Arg Ser Gln Leu Val Pro Val Arg Ala Leu Gly Leu Gly His
10                  15                  20                  25

Arg Ser Asp Glu Leu Val Arg Phe Arg Phe Cys Ser Gly Ser Cys Arg
                30                  35                  40

Arg Ala Arg Ser Pro His Asp Leu Ser Leu Ala Ser Leu Leu Gly Ala
                45                  50                  55

Gly Ala Leu Arg Pro Pro Gly Ser Arg Pro Val Ser Gln Pro Cys Cys
            60                  65                  70

Cys Arg Pro Thr Arg Tyr Glu Ala Val Ser Phe Met Asp Val Asn Ser
            75                  80                  85

Thr Trp Arg Thr Val Asp Arg Leu Ser Ala Thr Ala Cys Gly Cys Leu
90                  95                  100                 105

Gly

<210> SEQ ID NO 28
<211> LENGTH: 143
<212> TYPE: PRT
<213> ORGANISM: artificial sequence
<220> FEATURE:
<223> OTHER INFORMATION: deltapro human NBN104

<400> SEQUENCE: 28

Met Glu Leu Gly Leu Gly Gly Leu Ser Thr Leu Ser His Cys Pro Trp
1               5                   10                  15
```

```
Pro Arg Arg Gln Pro Ala Leu Trp Pro Thr Leu Ala Ala Leu Ala Leu
            20                  25                  30

Leu Ser Ser Val Ala Glu Ala Ala Gly Ala Arg Gly Cys Arg Leu
        35                  40                  45

Arg Ser Gln Leu Val Pro Val Arg Ala Leu Gly Leu Gly His Arg Ser
        50                  55                  60

Asp Glu Leu Val Arg Phe Arg Phe Cys Ser Gly Ser Cys Arg Arg Ala
65                  70                  75                  80

Arg Ser Pro His Asp Leu Ser Leu Ala Ser Leu Leu Gly Ala Gly Ala
                85                  90                  95

Leu Arg Pro Pro Pro Gly Ser Arg Pro Val Ser Gln Pro Cys Cys Arg
            100                 105                 110

Pro Thr Arg Tyr Glu Ala Val Ser Phe Met Asp Val Asn Ser Thr Trp
            115                 120                 125

Arg Thr Val Asp Arg Leu Ser Ala Thr Ala Cys Gly Cys Leu Gly
            130                 135                 140

<210> SEQ ID NO 29
<211> LENGTH: 141
<212> TYPE: PRT
<213> ORGANISM: artificial sequence
<220> FEATURE:
<223> OTHER INFORMATION: deltapro human NBN102
<220> FEATURE:
<221> NAME/KEY: SIGNAL
<222> LOCATION: (1)..(39)
<223> OTHER INFORMATION:
<220> FEATURE:
<221> NAME/KEY: mat_peptide
<222> LOCATION: (40)..()
<223> OTHER INFORMATION:

<400> SEQUENCE: 29

Met Glu Leu Gly Leu Gly Gly Leu Ser Thr Leu Ser His Cys Pro Trp
                -35                 -30                 -25

Pro Arg Arg Gln Pro Ala Leu Trp Pro Thr Leu Ala Ala Leu Ala Leu
            -20                 -15                 -10

Leu Ser Ser Val Ala Glu Ala Gly Ala Arg Gly Cys Arg Leu Arg Ser
        -5                  -1  1                   5

Gln Leu Val Pro Val Arg Ala Leu Gly Leu Gly His Arg Ser Asp Glu
10                  15                  20                  25

Leu Val Arg Phe Arg Phe Cys Ser Gly Ser Cys Arg Arg Ala Arg Ser
            30                  35                  40

Pro His Asp Leu Ser Leu Ala Ser Leu Leu Gly Ala Gly Ala Leu Arg
            45                  50                  55

Pro Pro Pro Gly Ser Arg Pro Val Ser Gln Pro Cys Cys Arg Pro Thr
        60                  65                  70

Arg Tyr Glu Ala Val Ser Phe Met Asp Val Asn Ser Thr Trp Arg Thr
        75                  80                  85

Val Asp Arg Leu Ser Ala Thr Ala Cys Gly Cys Leu Gly
90                  95                  100

<210> SEQ ID NO 30
<211> LENGTH: 138
<212> TYPE: PRT
<213> ORGANISM: artificial sequence
<220> FEATURE:
<223> OTHER INFORMATION: deltapro human NBN99
<220> FEATURE:
<221> NAME/KEY: SIGNAL
```

```
<222> LOCATION: (1)..(39)
<223> OTHER INFORMATION:
<220> FEATURE:
<221> NAME/KEY: mat_peptide
<222> LOCATION: (40)..()
<223> OTHER INFORMATION:

<400> SEQUENCE: 30

Met Glu Leu Gly Leu Gly Gly Leu Ser Thr Leu Ser His Cys Pro Trp
            -35                 -30                 -25

Pro Arg Arg Gln Pro Ala Leu Trp Pro Thr Leu Ala Ala Leu Ala Leu
        -20                 -15                 -10

Leu Ser Ser Val Ala Glu Ala Gly Cys Arg Leu Arg Ser Gln Leu Val
        -5                  -1   1               5

Pro Val Arg Ala Leu Gly Leu Gly His Arg Ser Asp Glu Leu Val Arg
 10              15                  20                  25

Phe Arg Phe Cys Ser Gly Ser Cys Arg Ala Arg Ser Pro His Asp
                30                  35                  40

Leu Ser Leu Ala Ser Leu Leu Gly Ala Gly Ala Leu Arg Pro Pro Pro
            45                  50                  55

Gly Ser Arg Pro Val Ser Gln Pro Cys Cys Arg Pro Thr Arg Tyr Glu
            60                  65                  70

Ala Val Ser Phe Met Asp Val Asn Ser Thr Trp Arg Thr Val Asp Arg
        75                  80                  85

Leu Ser Ala Thr Ala Cys Gly Cys Leu Gly
 90                  95

<210> SEQ ID NO 31
<211> LENGTH: 159
<212> TYPE: PRT
<213> ORGANISM: artificial sequence
<220> FEATURE:
<223> OTHER INFORMATION: Murin IgSP- human NBN140
<220> FEATURE:
<221> NAME/KEY: SIGNAL
<222> LOCATION: (1)..(19)
<223> OTHER INFORMATION:
<220> FEATURE:
<221> NAME/KEY: mat_peptide
<222> LOCATION: (20)..()
<223> OTHER INFORMATION:

<400> SEQUENCE: 31

Met Lys Cys Ser Trp Val Ile Phe Phe Leu Met Ala Val Val Thr Gly
            -15                 -10                 -5

Val Asn Ser Pro Pro Gln Pro Ser Arg Pro Ala Pro Pro Pro
        -1   1               5                   10

Ala Pro Pro Ser Ala Leu Pro Arg Gly Gly Arg Ala Ala Arg Ala Gly
            15                  20                  25

Gly Pro Gly Ser Arg Ala Arg Ala Ala Gly Ala Arg Gly Cys Arg Leu
 30                  35                  40                  45

Arg Ser Gln Leu Val Pro Val Arg Ala Leu Gly Leu Gly His Arg Ser
            50                  55                  60

Asp Glu Leu Val Arg Phe Arg Phe Cys Ser Gly Ser Cys Arg Arg Ala
            65                  70                  75

Arg Ser Pro His Asp Leu Ser Leu Ala Ser Leu Leu Gly Ala Gly Ala
        80                  85                  90

Leu Arg Pro Pro Pro Gly Ser Arg Pro Val Ser Gln Pro Cys Cys Arg
 95                  100                 105

Pro Thr Arg Tyr Glu Ala Val Ser Phe Met Asp Val Asn Ser Thr Trp
```

```
                110                 115                 120                 125
Arg Thr Val Asp Arg Leu Ser Ala Thr Ala Cys Gly Cys Leu Gly
            130                 135                 140

<210> SEQ ID NO 32
<211> LENGTH: 132
<212> TYPE: PRT
<213> ORGANISM: artificial sequence
<220> FEATURE:
<223> OTHER INFORMATION: Murin IgSP- human NBN113
<220> FEATURE:
<221> NAME/KEY: SIGNAL
<222> LOCATION: (1)..(19)
<223> OTHER INFORMATION:
<220> FEATURE:
<221> NAME/KEY: mat_peptide
<222> LOCATION: (20)..()
<223> OTHER INFORMATION:

<400> SEQUENCE: 32

Met Lys Cys Ser Trp Val Ile Phe Phe Leu Met Ala Val Val Thr Gly
            -15                 -10                 -5

Val Asn Ser Ala Gly Gly Pro Gly Ser Arg Ala Arg Ala Ala Gly Ala
        -1  1               5                  10

Arg Gly Cys Arg Leu Arg Ser Gln Leu Val Pro Val Arg Ala Leu Gly
        15                  20                  25

Leu Gly His Arg Ser Asp Glu Leu Val Arg Phe Arg Phe Cys Ser Gly
30                  35                  40                  45

Ser Cys Arg Arg Ala Arg Ser Pro His Asp Leu Ser Leu Ala Ser Leu
            50                  55                  60

Leu Gly Ala Gly Ala Leu Arg Pro Pro Pro Gly Ser Arg Pro Val Ser
            65                  70                  75

Gln Pro Cys Cys Arg Pro Thr Arg Tyr Glu Ala Val Ser Phe Met Asp
            80                  85                  90

Val Asn Ser Thr Trp Arg Thr Val Asp Arg Leu Ser Ala Thr Ala Cys
            95                  100                 105

Gly Cys Leu Gly
110

<210> SEQ ID NO 33
<211> LENGTH: 125
<212> TYPE: PRT
<213> ORGANISM: artificial sequence
<220> FEATURE:
<223> OTHER INFORMATION: Murin IgSP- human NBN106
<220> FEATURE:
<221> NAME/KEY: SIGNAL
<222> LOCATION: (1)..(19)
<223> OTHER INFORMATION:
<220> FEATURE:
<221> NAME/KEY: mat_peptide
<222> LOCATION: (20)..()
<223> OTHER INFORMATION:

<400> SEQUENCE: 33

Met Lys Cys Ser Trp Val Ile Phe Phe Leu Met Ala Val Val Thr Gly
            -15                 -10                 -5

Val Asn Ser Ala Arg Ala Ala Gly Ala Arg Gly Cys Arg Leu Arg Ser
        -1  1               5                  10

Gln Leu Val Pro Val Arg Ala Leu Gly Leu Gly His Arg Ser Asp Glu
        15                  20                  25

Leu Val Arg Phe Arg Phe Cys Ser Gly Ser Cys Arg Arg Ala Arg Ser
30                  35                  40                  45
```

```
Pro His Asp Leu Ser Leu Ala Ser Leu Leu Gly Ala Gly Ala Leu Arg
            50                  55                  60

Pro Pro Pro Gly Ser Arg Pro Val Ser Gln Pro Cys Cys Arg Pro Thr
            65                  70                  75

Arg Tyr Glu Ala Val Ser Phe Met Asp Val Asn Ser Thr Trp Arg Thr
            80                  85                  90

Val Asp Arg Leu Ser Ala Thr Ala Cys Gly Cys Leu Gly
            95                 100                 105

<210> SEQ ID NO 34
<211> LENGTH: 123
<212> TYPE: PRT
<213> ORGANISM: artificial sequence
<220> FEATURE:
<223> OTHER INFORMATION: Murin IgSP- human NBN1104
<220> FEATURE:
<221> NAME/KEY: SIGNAL
<222> LOCATION: (1)..(19)
<223> OTHER INFORMATION:
<220> FEATURE:
<221> NAME/KEY: mat_peptide
<222> LOCATION: (20)..()
<223> OTHER INFORMATION:

<400> SEQUENCE: 34

Met Lys Cys Ser Trp Val Ile Phe Phe Leu Met Ala Val Val Thr Gly
                -15                 -10                  -5

Val Asn Ser Ala Ala Gly Ala Arg Gly Cys Arg Leu Arg Ser Gln Leu
        -1   1               5                  10

Val Pro Val Arg Ala Leu Gly Leu Gly His Arg Ser Asp Glu Leu Val
            15                  20                  25

Arg Phe Arg Phe Cys Ser Gly Ser Cys Arg Arg Ala Arg Ser Pro His
30                  35                  40                  45

Asp Leu Ser Leu Ala Ser Leu Leu Gly Ala Gly Ala Leu Arg Pro Pro
            50                  55                  60

Pro Gly Ser Arg Pro Val Ser Gln Pro Cys Cys Arg Pro Thr Arg Tyr
            65                  70                  75

Glu Ala Val Ser Phe Met Asp Val Asn Ser Thr Trp Arg Thr Val Asp
        80                  85                  90

Arg Leu Ser Ala Thr Ala Cys Gly Cys Leu Gly
            95                 100

<210> SEQ ID NO 35
<211> LENGTH: 121
<212> TYPE: PRT
<213> ORGANISM: artificial sequence
<220> FEATURE:
<223> OTHER INFORMATION: Murin IgSP- human NBN102
<220> FEATURE:
<221> NAME/KEY: SIGNAL
<222> LOCATION: (1)..(19)
<223> OTHER INFORMATION:
<220> FEATURE:
<221> NAME/KEY: mat_peptide
<222> LOCATION: (20)..()
<223> OTHER INFORMATION:

<400> SEQUENCE: 35

Met Lys Cys Ser Trp Val Ile Phe Phe Leu Met Ala Val Val Thr Gly
                -15                 -10                  -5

Val Asn Ser Gly Ala Arg Gly Cys Arg Leu Arg Ser Gln Leu Val Pro
        -1   1               5                  10
```

-continued

```
Val Arg Ala Leu Gly Leu Gly His Arg Ser Asp Glu Leu Val Arg Phe
 15              20                  25
Arg Phe Cys Ser Gly Ser Cys Arg Arg Ala Arg Ser Pro His Asp Leu
 30              35                  40                  45
Ser Leu Ala Ser Leu Gly Ala Gly Ala Leu Arg Pro Pro Gly
                 50                  55                  60
Ser Arg Pro Val Ser Gln Pro Cys Cys Arg Pro Thr Arg Tyr Glu Ala
                 65                  70                  75
Val Ser Phe Met Asp Val Asn Ser Thr Trp Arg Thr Val Asp Arg Leu
                 80                  85                  90
Ser Ala Thr Ala Cys Gly Cys Leu Gly
                 95                 100
```

<210> SEQ ID NO 36
<211> LENGTH: 118
<212> TYPE: PRT
<213> ORGANISM: artificial sequence
<220> FEATURE:
<223> OTHER INFORMATION: Murin IgSP- human NBN99
<220> FEATURE:
<221> NAME/KEY: SIGNAL
<222> LOCATION: (1)..(19)
<223> OTHER INFORMATION:
<220> FEATURE:
<221> NAME/KEY: mat_peptide
<222> LOCATION: (20)..()
<223> OTHER INFORMATION:

<400> SEQUENCE: 36

```
Met Lys Cys Ser Trp Val Ile Phe Phe Leu Met Ala Val Val Thr Gly
                -15                 -10                  -5
Val Asn Ser Gly Cys Arg Leu Arg Ser Gln Leu Val Pro Val Arg Ala
         -1  1               5                  10
Leu Gly Leu Gly His Arg Ser Asp Glu Leu Val Arg Phe Arg Phe Cys
 15                  20                  25
Ser Gly Ser Cys Arg Arg Ala Arg Ser Pro His Asp Leu Ser Leu Ala
 30                  35                  40                  45
Ser Leu Leu Gly Ala Gly Ala Leu Arg Pro Pro Gly Ser Arg Pro
                 50                  55                  60
Val Ser Gln Pro Cys Cys Arg Pro Thr Arg Tyr Glu Ala Val Ser Phe
                 65                  70                  75
Met Asp Val Asn Ser Thr Trp Arg Thr Val Asp Arg Leu Ser Ala Thr
                 80                  85                  90
Ala Cys Gly Cys Leu Gly
                 95
```

<210> SEQ ID NO 37
<211> LENGTH: 492
<212> TYPE: DNA
<213> ORGANISM: artificial sequence
<220> FEATURE:
<223> OTHER INFORMATION: deltapro human 113 nucleic acid sequence

<400> SEQUENCE: 37

```
tataggatcc gccaccatgg aacttggact tggaggcctc tccacgctgt cccactgccc    60
ctggcctagg cggcagcctg ccctgtggcc caccctggcc gctctggctc tgctgagcag   120
cgtcgcagag gccgctgggg gcccgggcag ccgcgctcgg gcagcggggg cgcggggctg   180
ccgcctgcgc tcgcagctgg tgccggtgcg cgcgctcggc ctgggccacc gctccgacga   240
gctggtgcgt ttccgcttct gcagcggctc ctgccgccgc gcgcgctctc cacacgacct   300
```

```
cagcctggcc agcctactgg gcgccggggc cctgcgaccg ccccgggct cccggcccgt      360 cagccagccc tgctgccgac ccacgcgcta cgaagcggtc tccttcatgg acgtcaacag      420
cacctggaga accgtggacc gcctctccgc caccgcctgc ggctgcctgg gctgagggct      480
cgctcgagta ta                                                         492
```